(12) United States Patent
Bernardon

(10) Patent No.: US 6,368,608 B1
(45) Date of Patent: Apr. 9, 2002

(54) POLYAROMATIC PROPYNYL COMPOUNDS AND PHARMACEUTICAL/COSMETIC COMPOSITIONS COMPRISED THEREOF

(75) Inventor: Jean-Michel Bernardon, Le Rouret (FR)

(73) Assignee: Centre International de Recherche Dermatologiques Galderma (C.I.R.D.), Valbonne (FR)

( * ) Notice: Subject to any disclaimer, the term of this patent is extended or adjusted under 35 U.S.C. 154(b) by 0 days.

(21) Appl. No.: 09/699,379

(22) Filed: Oct. 31, 2000

Related U.S. Application Data

(62) Division of application No. 08/944,566, filed on Oct. 6, 1997, now Pat. No. 6,162,445, which is a division of application No. 08/357,024, filed on Dec. 15, 1994, now Pat. No. 5,716,624.

(30) Foreign Application Priority Data

Dec. 15, 1993 (FR) .............................................. 93 15067

(51) Int. Cl.[7] .......................... A61K 7/48; A61K 31/192
(52) U.S. Cl. ....................... 424/401; 514/544; 514/549; 514/568; 514/622; 514/700; 514/708; 514/710; 514/731
(58) Field of Search .......................... 424/401; 514/544, 514/549, 568, 622, 700, 708, 710, 731

(56) References Cited

U.S. PATENT DOCUMENTS

| | | | |
|---|---|---|---|
| 4,703,110 A | 10/1987 | Shudo ........................ | 534/566 |
| 5,223,518 A | 6/1993 | Dinerstein et al. .......... | 514/345 |
| 5,248,825 A | 9/1993 | Dinerstein et al. .......... | 564/305 |

FOREIGN PATENT DOCUMENTS

| | | |
|---|---|---|
| EP | 0170105 | 2/1986 |
| EP | 0401517 | 12/1990 |
| EP | 0476645 | 3/1992 |
| EP | 0476658 | 3/1992 |
| EP | 0514264 | 11/1992 |
| WO | 9220643 | 11/1992 |

OTHER PUBLICATIONS

Chemical Abstracts CA97:215237w (1982).
Chemical Abstracts CA98:178949c (1982).
*Chemical Letters*, vol. 10:1551–1557 (1982).

*Primary Examiner*—Richard Raymond
(74) *Attorney, Agent, or Firm*—Burns, Doane, Swecker & Mathis, L.L.P.

(57) ABSTRACT

Novel pharmaceutically/cosmetically-active polyaromatic propynyl compounds have the structural formula (I):

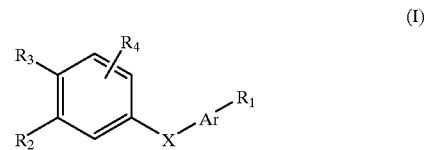

in which X is one of the radicals:

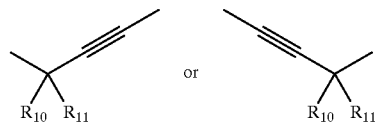

and are useful for the treatment of a wide variety of disease states, whether human or veterinary, for example dermatological, rheumatic, respiratory, cardiovascular and ophthalmological disorders, as well as for the treatment of mammalian skin and hair conditions/disorders.

39 Claims, 3 Drawing Sheets

POLYAROMATIC PROPYNYL COMPOUNDS AND PHARMACEUTICAL/COSMETIC COMPOSITIONS COMPRISED THEREOF

CROSS-REFERENCE TO COMPANION APPLICATIONS

This application is a divisional of application Ser. No. 08/944,566, filed Oct. 6, 1997, now U.S. Pat. No. 6,162,445, which is a divisional of application Ser. No. 08/357,024, filed Dec. 15, 1994 now U.S. Pat. No. 5,716,624.4

BACKGROUND OF THE INVENTION

Field of the Invention

The present invention relates to novel polyaromatic propynyl compounds and to pharmaceutical/cosmetic compositions comprised thereof; the subject compounds are especially useful in human or veterinary medicine, or alternatively in cosmetic compositions.

SUMMARY OF THE INVENTION

The compounds according to the invention display marked activity in the fields of cell differentiation and proliferation, and are particularly useful in the topical and systemic treatment of dermatological conditions associated with a keratinization disorder, dermatological conditions (and the like) including an inflammatory and/or immunoallergic component, and dermal or epidermal proliferations, whether benign or malignant. The subject compounds can, in addition, be used for the treatment of degeneration diseases of the connective tissue, for combating skin aging, whether photoinduced or chronologic, and for treating cicatrization disorders. They are also useful for ophthalmological applications, especially for the treatment of corneopathies.

The compounds according to this invention can also be formulated into cosmetic compositions for body and hair care.

Briefly, the polyaromatic propynyl compounds according to this invention have the following structural formula (I):

(I)

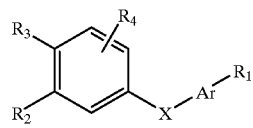

in which X is one of the radicals:

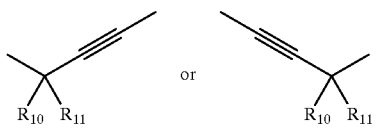

wherein $R_{10}$ and $R_{11}$ are as defined below; Ar is a radical selected from among those of the following formulae (a)–(e):

(a)
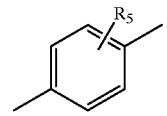

(b)
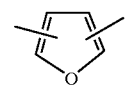

(c)
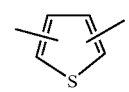

(d)
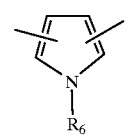

(e)
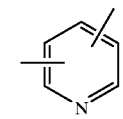

wherein $R_5$ and $R_6$ are as defined below; $R_1$ is (i) a hydrogen atom, (ii) a radical —$CH_3$, (iii) a radical —$CH_2$—O—$R_6$, (iv) a radical —O—$R_6$, (v) a radical —CO—$R_7$, or (vi) a radical —$S(O)_tR_9$ wherein $R_6$, $R_7$, $R_9$ and t are as defined below; $R_2$ and $R_3$, which may be identical or different, are each a hydrogen atom, a linear or branched alkyl radical having from 1 to 20 carbon atoms, a radical —$OR_6$ or a radical —$SR_6$, wherein $R_6$ is as defined below, with the proviso that $R_2$ and $R_3$ may together form, with the carbon atoms from which they depend, a 5-or 6-membered ring optionally substituted by methyl groups and/or optionally interrupted by an oxygen or sulfur atom; $R_4$ is a hydrogen atom, a halogen atom, a lower alkyl radical or a radical —$OR_6$ wherein $R_6$ is as defined below; $R_5$ has the definition of $R_4$, with the proviso that $R_4$ and $R_5$ may be identical or different; $R_6$ is a hydrogen atom, a lower alkyl radical or a radical —CO—$R_9$ wherein $R_9$ is as defined below and further wherein the radicals $R_6$ may be identical or different; $R_7$ is (a) a hydrogen atom, (b) a lower alkyl radical, (c) a radical of the formula:

$$\diagdown N \diagup^{R''}_{R'}$$

wherein R' and R" are as defined below, or (d) a radical —$OR_8$ wherein $R_8$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue, or an amino acid or peptide residue; $R_9$ is a lower alkyl radical; $R_{10}$ is a hydrogen atom, a lower alkyl radical, or a radical —$OR_6$; $R_{11}$ is a radical —$OR_6$; R' and R", which may be identical or different, are each a hydrogen atom, a lower alkyl radical, a mono or polyhydroxyalkyl radical, an optionally substituted aryl radical or an amino acid or peptide or sugar residue, with the proviso that R' and R" may together form, with the nitrogen atom from which they depend, a heterocycle; t is an integer equal to 0, 1 or 2; and with the further proviso that the radicals $R_{10}$ and $R_{11}$ may together form a single oxo group of the formula =O.

This invention also features the salts of the compounds of formula (I) in the event that $R_1$ is a carboxylic acid functional group, as well as the optical and geometric isomers thereof. When the compounds according to the invention are in the form of salts, they are preferably salts of an alkali or alkaline earth metal, or, alternatively, of zinc or of an organic amine.

DETAILED DESCRIPTION OF BEST MODE AND PREFERRED EMBODIMENTS OF THE INVENTION

Figure 1:
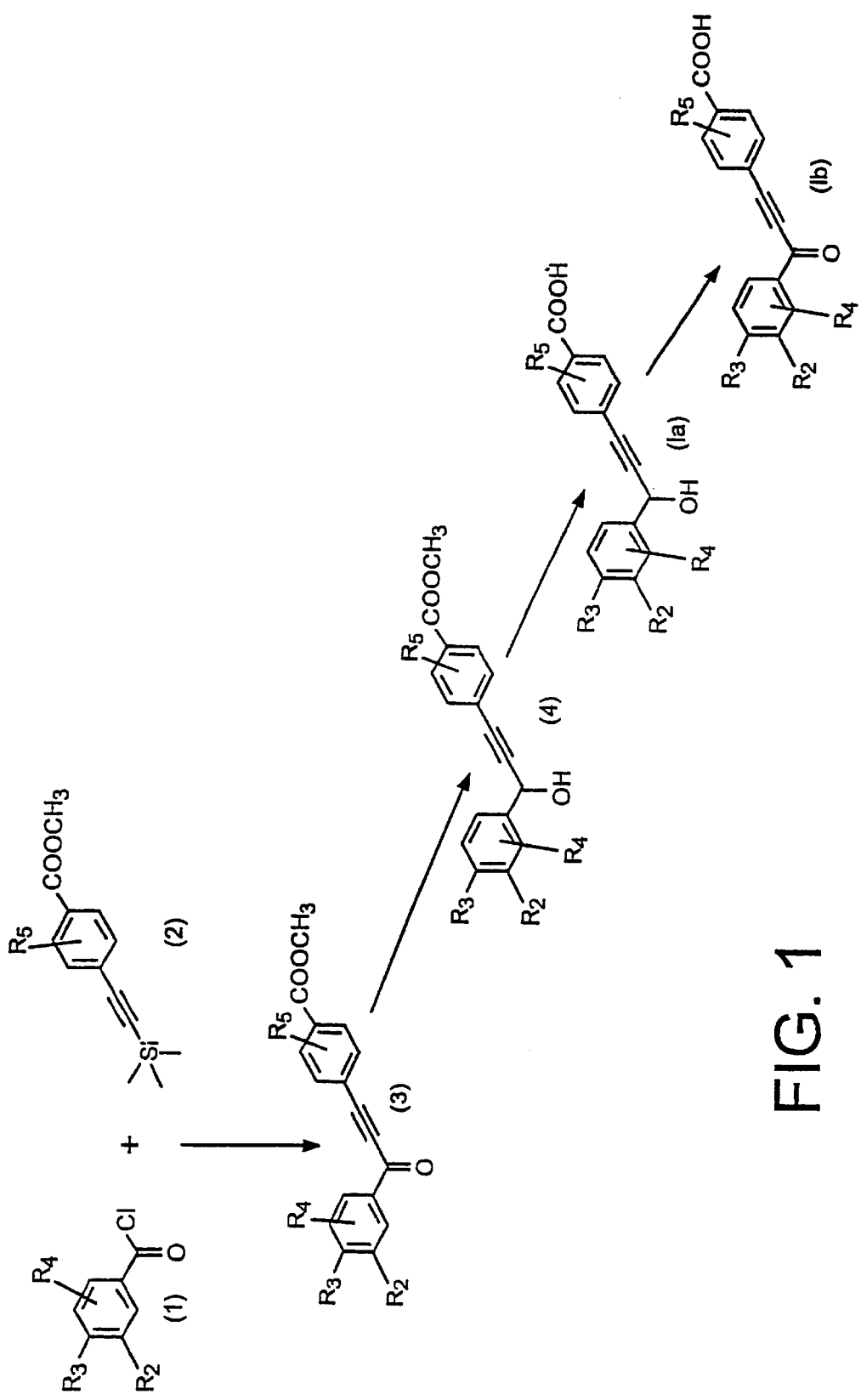
FIGS. 1, 2 and 3 are reaction schemes/mechanism illustrating syntheses for the preparation of the polyaromatic propynyl compounds according to the present invention.

More particularly according to the present invention, by "lower alkyl radical" is intended an alkyl radical having from 1 to 6 carbon atoms, preferably methyl, ethyl, isopropyl, butyl, tert-butyl and hexyl radicals.

By "linear or branched alkyl radical having from 1 to 20 carbon atoms" is preferably intended methyl, ethyl, propyl, 2-ethylhexyl, octyl, dodecyl, hexadecyl and octadecyl radicals.

By "monohydroxyalkyl radical" is intended a radical preferably having 2 or 3 carbon atoms, especially a 2-hydroxyethyl, 2-hydroxypropyl or 3-hydroxypropyl radical.

By "polyhydroxyalkyl radical" is intended a radical preferably having 3 to 6 carbon atoms and 2 to 5 hydroxyl groups, such as 2,3-dihydroxypropyl, 2,3,4-trihydroxybutyl or 2,3,4,5-tetrahydroxypentyl radicals, or a pentaerythritol residue.

By "aryl radical" is preferably intended a phenyl radical optionally substituted by at least one halogen atom, or a hydroxyl or nitro functional group.

By "aralkyl radical" is preferably intended a benzyl or phenethyl radical optionally substituted by at least one halogen atom, or a hydroxyl or nitro functional group.

By "alkenyl radical" is intended a radical preferably having from 1 to 5 carbon atoms and one or more sites of ethylenic unsaturation, such as, more particularly, the allyl radical.

By "sugar residue" is intended a residue derived especially from glucose, galactose or mannose, or alternatively from glucuronic acid.

By "amino acid residue" is especially intended a residue derived from lysine, glycine or aspartic acid, and by "peptide residue" is more particularly intended a dipeptide or tripeptide residue prepared via the combination of amino acids.

Lastly, by "heterocycle" is preferably intended a piperidino, morpholino, pyrrolidino or piperazino radical, optionally substituted at the 4-position by a $C_1$–$C_6$ alkyl radical or a mono- or polyhydroxyalkyl radical as defined above.

When $R_4$ and $R_5$ in formula (I) represent a halogen atom, it is preferably a fluorine, chlorine or bromine atom.

Among the compounds of formula (I) according to the present invention, particularly representative are the following:

Methyl 4-[3-oxo-(5,6,7,8-tetrahydro-5,5,8,8-tetramethyl-2-naphthyl)-1-propynyl]benzoate;
Methyl 4-[3-hydroxy-3-(5,6,7,8-tetrahydro-5,5,8,8-tetramethyl-2-naphthyl)-1-propynyl]benzoate;
4-[3-Hydroxy-3-(5,6,7,8-tetrahydro-5,5,8,8-tetramethyl-2-naphthyl)-1-propynyl]benzoic acid;
4-[3-Oxo-3-(5,6,7,8-tetrahydro-5,5,8,8-tetramethyl-2-naphthyl)-1-propynyl]benzoic acid;
2-Hydroxy-4-[3-oxo-3-(5,6,7,8-tetrahydro-5,5,8,8-tetramethyl-2-naphthyl)-1-propynyl]benzoic acid;
Methyl 2-hydroxy-4-[3-hydroxy-3-(5,6,7,8-tetrahydro-5,5,8,8-tetramethyl-2-naphthyl)-1-propynyl]benzoate;
2-Hydroxy-4-[3-hydroxy-3-(5,6,7,8-tetrahydro-5,5,8,8-tetramethyl-2-naphthyl)-1-propynyl]benzoic acid;
2-Hydroxy-4-[3-oxo-(3-tert-butyl-4-methoxyphenyl)-1-propynyl]benzoic acid;
4-[1-Oxo-3-(5,6,7,8-tetrahydro-5,5,8,8-tetramethyl-2-naphthyl)-2-propynyl]benzoic acid;
4-[1-Hydroxy-3-(5,6,7,8-tetrahydro-5,5,8,8-tetramethyl-2-naphthyl)-2-propynyl]benzoic acid;
Methyl 2-hydroxy-4-[3-hydroxy-3-(4,4-dimethylthiochroman-6-yl)-1-propynyl]benzoate;
2-Hydroxy-4-(3-oxo-3-(4,4-dimethylthiochroman-6-yl)-1-propynyl]benzoic acid;
4-[3-Hydroxy-3-(3-tert-butyl-4-methoxyphenyl)-1-propynyl]benzoic acid;
Methyl N-methyl-4-[3-hydroxy-3-(5,6,7,8-tetrahydro-5,5,8,8-tetramethyl-2-naphthyl)-1-propynyl]-2-pyrrolecarboxylate;
N-Methyl-4-[3-hydroxy-3-(5,6,7,8-tetrahydro-5,5,8,8-tetramethyl-2-napthyl)-1-propynyl]-2-pyrrolecarboxylic acid;
Methyl 4-[3-hydroxy-3-(5,6,7,8-tetrahydro-5,5,8,8-tetramethyl-2-napthyl)-1-propynyl]-2-pyrrolecarboxylate;
Methyl 2-hydroxy-4-[3-hydroxy-3-(4,4-dimethylthiochroman-7-yl)-1-propynyl]benzoate;
4-[1-Hydroxy-3-(4,4-dimethylthiochroman-6-yl)-2-propynyl]benzoic acid;
2-Hydroxy-4-[3-hydroxy-3-(4,4-dimethylthiochroman-6-yl)-1-propynyl]benzoic acid;
2-Hydroxy-4-[3-hydroxy-3-(4,4-dimethylthiochroman-7-yl)-1-propynyl]benzoic acid;
(+)-Isomer of methyl 4-(3-hydroxy-3-(5,6,7,8-tetrahydro-5,5,8,8-tetramethyl-2-naphthyl)-1-propynyl]benzoate;
(−)-Isomer of 4-[3-hydroxy-3-(5,6,7,8-tetrahydro-5,5,8,8-tetramethyl-2-naphthyl)-1-propynyl]benzoic acid;
(+)-Isomer of methyl 2-hydroxy-4-[3-hydroxy-3-(5,6,7,8-tetrahydro-5,5,8,8-tetramethyl-2-naphthyl)-1-propynyl]benzoate;
(−)-Isomer of 2-hydroxy-4-[3-hydroxy-3-(5,6,7,8-tetrahydro-5,5,8,8-tetramethyl-2-naphthyl)-1-propynyl]benzoic acid;
(−)-Isomer of methyl 4-[3-hydroxy-3-(5,6,7,8-tetrahydro-5,5,8,8-tetramethyl-2-naphthyl)-1-propynyl]benzoate;
(−)-Isomer of methyl 2-hydroxy-4-[3-hydroxy-3-(5,6,7,8-tetrahydro-5,5,8,8-tetramethyl-2-naphthyl)-1-propynyl]benzoate;
(+)-Isomer of 4-[3-hydroxy-3-(5,6,7,8-tetrahydro-5,5,8,8-tetramethyl-2-naphthyl)-1-propynyl]benzoic acid;
(+)-Isomer of 2-hydroxy-4-[3-hydroxy-3-(5,6,7,8-tetrahydro-5,5,8,8-tetramethyl-2-naphthyl)-1-propynyl]benzoic acid;
Methyl 2-hydroxy-4-[3-hydroxy-3-methyl-3-(5,6,7,8-tetrahydro-5,5,8,8-tetramethyl-2-naphthyl)-1-propynyl]benzoate;
2-Hydroxy-4-[3-hydroxy-3-methyl-3-(5,6,7,8-tetrahydro-5,5,8,8-tetramethyl-2-naphthyl)-1-propynyl]benzoic acid;

2-Methoxy-4-[3-hydroxy-3-(5,6,7,8-tetrahydro-5,5,8,8-tetramethyl-2-naphthyl)-1-propynyl]benzoic acid;

4-[3-Hydroxy-3-(5,6,7,8-tetrahydro-5,5,8,8-tetramethyl-2-naphthyl)-1-propynyl]benzaldehyde;

4-[3-Hydroxy-3-(5,6,7,8-tetrahydro-5,5,8,8-tetramethyl-2-naphthyl)-1-propynyl]benzyl acetate;

4-[3-Hydroxy-3-(5,6,7,8-tetrahydro-5,5,8,8-tetramethyl-2-naphthyl)-1-propynyl]benzene methanol;

4-[3-Hydroxy-3-(5,6,7,8-tetrahydro-5,5,8,8-tetramethyl-2-naphthyl)-1-propynyl]toluene;

4-[3-Hydroxy-3-(5,6,7,8-tetrahydro-3,5,5,8,8-pentamethyl-2-naphthyl)-1-propynyl]phenyl acetate;

4-[3-Hydroxy-3-(5,6,7,8-tetrahydro-3,5,5,8,8-pentamethyl-2-naphthyl)-1-propynyl]phenol;

4-[3-Hydroxy-3-(5,6,7,8-tetrahydro-5,5,8,8-tetramethyl-2-naphthyl)-1-propynyl]phenylsulfinylmethane;

4-[3-Hydroxy-3-(5,6,7,8-tetrahydro-5,5,8,8-tetramethyl-2-naphthyl)-1-propynyl]phenylsulfonylmethane;

N-Ethyl-4-[3-hydroxy-3-(5,6,7,8-tetrahydro-5,5,8,8-tetramethyl-2-naphthyl)-1-propynyl]benzamide;

N,N'-Diethyl-4-[3-hydroxy-3-(5,6,7,8-tetrahydro-5,5,8,8-tetramethyl-2-naphthyl)-1-propynyl]benzamide;

Morpholide of 4-[3-hydroxy-3-(5,6,7,8-tetrahydro-5,5,8,8-tetramethyl-2-naphthyl)-1-propynyl]benzoic acid;

Methyl 5-[3-hydroxy-3-(5,6,7,8-tetrahydro-5,5,8,8-tetramethyl-2-naphthyl)-1-propynyl]-2-thiophenecarboxylate;

Methyl 2-hydroxy-4-[3-hydroxy-(5,6,7,8-tetrahydro-3,5,5,8,8-pentamethyl-2-naphthyl)-1-propynyl]benzoate;

2-Hydroxy-4-[3-hydroxy-3-(5,6,7,8-tetrahydro-3,5,5,8,8-pentamethyl-2-naphthyl)-1-propynyl]benzoic acid;

Methyl 2-hydroxy-4-[3-hydroxy-3-(3-methoxy-5,6,7,8-tetrahydro-5,5,8,8-tetramethyl-2-naphthyl)-1-propynyl]benzoate;

2-Hydroxy-4-(3-hydroxy-3-(3-methoxy-5,6,7,8-tetrahydro-5,5,8,8-tetramethyl-2-naphthyl)-1-propynyl]benzoic acid;

4-[3-Hydroxy-3-(4,4-dimethylthiochroman-6-yl)-1-propynyl]benzoic acid;

4-[3-Hydroxy-3-(4,4-dimethylthiochroman-7-yl)-1-propynyl]benzoic acid;

Methyl 3-methyl-4-[3-hydroxy-3-(5,6,7,8-tetrahydro-5,5,8,8-tetramethyl-2-naphthyl)-1-propynyl]benzoate;

3-Methyl-4-[3-hydroxy-3-(5,6,7,8-tetrahydro-5,5,8,8-tetramethyl-2-naphthyl)-1-propynyl]benzoic acid;

2-Chloro-4-[3-hydroxy-3-(5,6,7,8-tetrahydro-5,5,8,8-tetramethyl-2-naphthyl)-1-propynyl]benzoic acid;

2-Acetoxy-4-[3-acetoxy-3-(5,6,7,8-tetrahydro-5,5,8,8-tetramethyl-2-naphthyl)-1-propynyl]benzoic acid;

Methyl 4-[3-hydroxy-3-(3-tert-butyl-4-propyloxyphenyl)-1-propynyl]benzoate;

Methyl 4-[3-hydroxy-3-(3-tert-butyl-4-hexyloxyphenyl)-1-propynyl]benzoate.

According to the present invention, the compounds of formula (I) which are more particularly preferred are those in which $R_5$ represents —OH, $R_7$ represents a radical $OR_8$ and $R_{11}$ represents a radical —$OR_6$.

Figure 2:
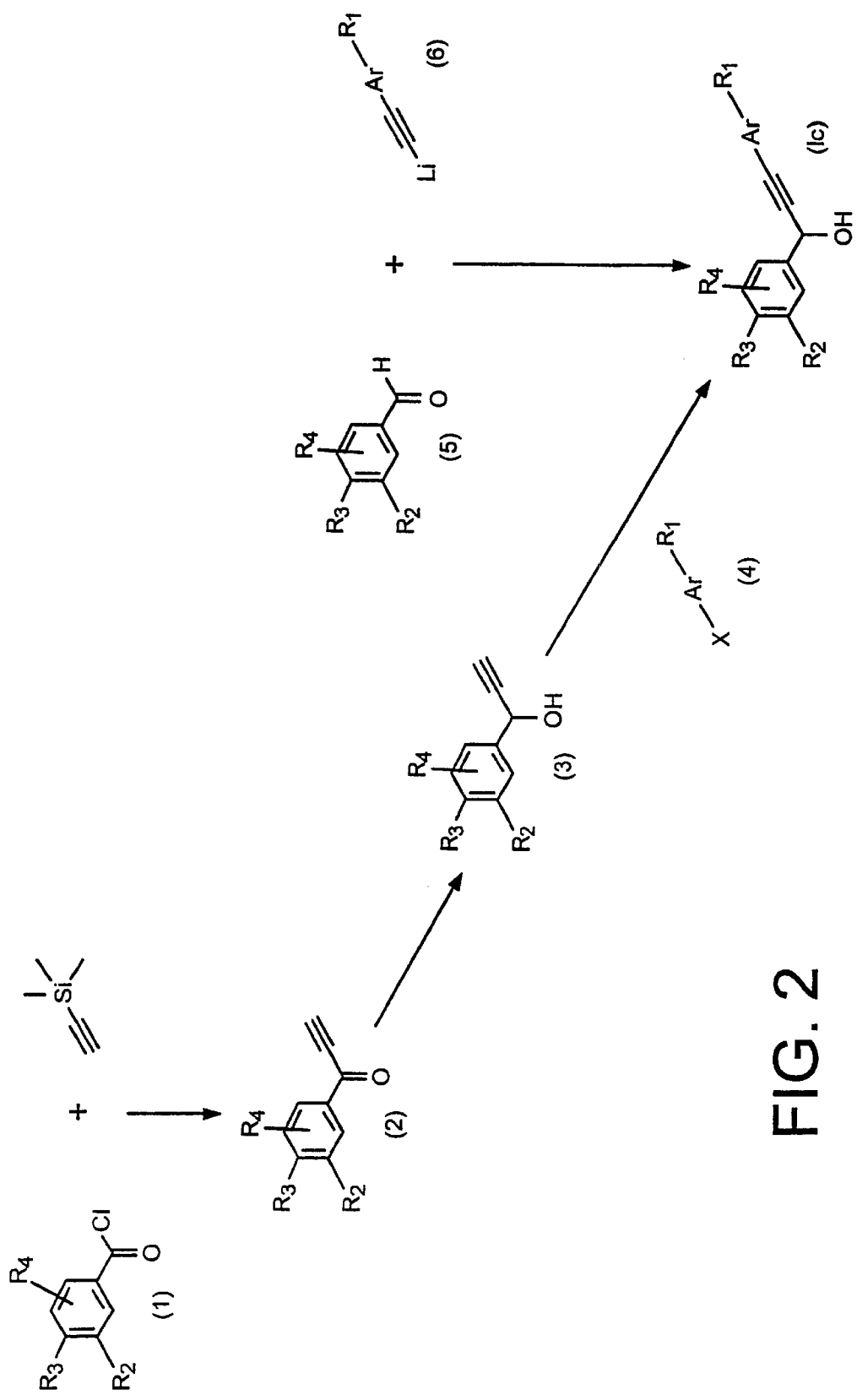
Figure 3:
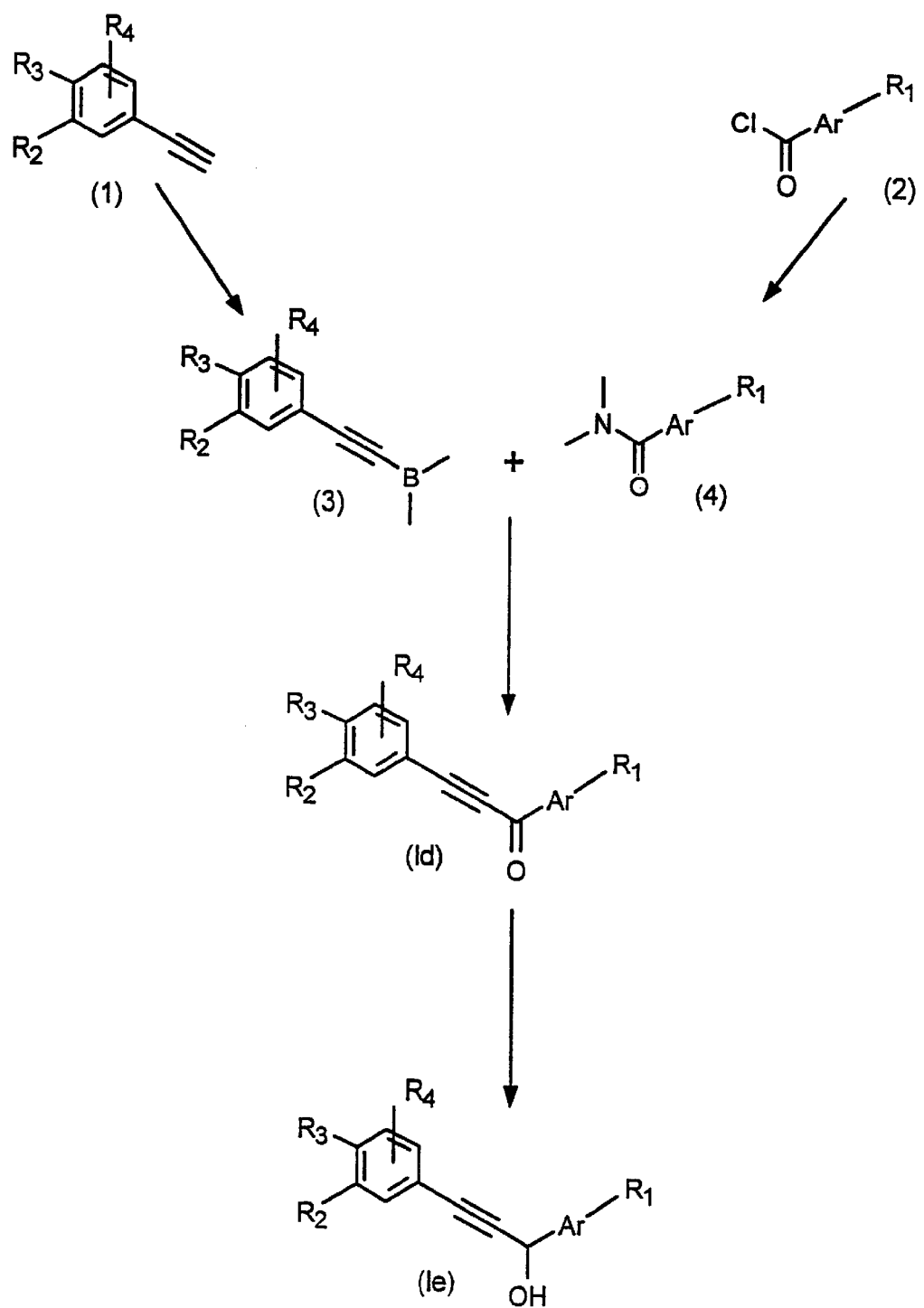

The present invention also features the processes for preparing the compounds of formula (I) via the reaction schemes or mechanisms illustrated in FIGS. 1, 2 and 3.

The intermediate of formula (Ia) can be prepared by a series of reactions comprising the reaction of a benzoyl chloride of formula (1) with an acetylene derivative of formula (2) in the presence of a Lewis acid (for example $AlCl_3$) in a chlorinated solvent, such as dichloromethane. The ketone (3) thus obtained is reduced to the alcohol (4) by reaction with an alkali metal hydride, such as sodium borohydride, in an alcoholic solvent (for example methanol).

Saponification of the ester functional group in the presence of a base, such as sodium or lithium hydroxide, in an alcoholic solvent or in THF then yields the intermediates of formula (Ia).

The intermediates of formula (Ib) are prepared by oxidation of the intermediate (Ia) in the presence of pyridinium dichromate or manganese oxide in an organic solvent such as dichloromethane.

The intermediates of formula (Ic) can be prepared by coupling a halogenated intermediate (4), preferably an iodinated or brominated compound, with an α-hydroxyacetylene compound (3) in the presence of a palladium catalyst [for example bis(triphenylphosphine) palladium(II) chloride] in a solvent such as triethylamine. The α-hydroxyacetylene intermediate (3) is prepared by reacting a benzoyl chloride of formula (1) with trimethylsilylacetylene in the presence of a Lewis acid (for example $AlCl_3$) in a chlorinated solvent and then reduction of the ketone obtained (2) with an alkali metal hydride (for example sodium borohydride) in an alcoholic solvent.

The intermediates of formula (Ic) can also be prepared when $R_1$ is other than —$COOR_8$ by reacting a lithium phenylacetylide of formula (6) with a benzaldehyde derivative of formula (5) in an organic solvent, such as ethyl ether or THF.

The intermediates of formula (Id) can be prepared by reacting a boron acetylide (3) (prepared in situ from lithium phenylacetylide and boron trifluoride at −78° C. in THF) with a tertiary benzamide of formula (4) in an organic solvent such as THF. The compounds of formula (Ie) are prepared by reduction of the preceding compound with an alkali metal hydride.

When $R_1$ represents a radical —COOH and $R_{10}$ and $R_{11}$ together form an oxo radical, the compounds are preferably prepared by protecting $R_1$ in the methyl, ethyl or allyl ester form, conversion to the free form being carried out in the presence of lithium hydroxide in THF.

The present invention also features therapeutic/pharmaceutical applications of the compounds of formula (I).

These compounds exhibit activity in the test for differentiation of mouse embryonic teratocarcinoma cells (F9) (*Cancer Research*, 43, p. 5268 (1983)) and/or in the test for inhibition of ornithine decarboxylase after induction with TPA in mice (*Cancer Research*, 38, p. 793–801 (1978)). These tests demonstrate the activities of the subject compounds for cell differentiation and proliferation applications, respectively.

The compounds according to the invention are particularly suitable in the following fields of therapy:

(1) for treating dermatological conditions associated with a keratinization disorder related to differentiation and to proliferation, especially for treating acne vulgaris or comedo-type, polymorphic or rosacea acnes, nodulocystic acne or acne conglobata, senile acnes, secondary acnes such as solar acne, acne medicamentosa or occupational acne;

(2) for treating other types of keratinization disorders, especially ichthyoses, ichthyosiform states, Darier's disease, keratoses palmaris and plantaris, leucoplakias and leucoplakia-like states, skin or mucous (buccal) lichen;

(3) for treating other dermatological conditions associated with a keratinization disorder manifesting an inflammatory and/or immunoallergic component, and, especially, all forms of psoriasis, whether cutaneous, mucous or ungual, and even arthropathic psoriasis, or, alternatively, skin atopy, such as eczema or respiratory atopy or alternatively gingival hypertrophy; the compounds can also be used for treating inflammatory conditions not exhibiting keratinization disorder;

(4) for treating all dermal or epidermal proliferations, whether benign or malignant, whether or not they are of viral origin, such as verruca vulgaris, verruca plana and epidermodysplasia verruciformis, oral or florid papillomatoses and proliferations which can be induced by ultraviolet radiation, especially in the case of baso- and spinocellular epitheliomas;

(5) for treating other dermatological disorders such as bullous dermatoses and collagen diseases;

(6) for treating certain ophthalmological disorders, especially corneopathies;

(7) for repairing or combating skin aging, whether photoinduced or chronologic, or to reduce pigmentations and actinic keratoses, or all pathologies associated with chronologic or actinic aging;

(8) for preventing or curing the stigmas of epidermal and/or dermal atrophy induced by local or systolic corticosteroids, or any other form of skin atrophy;

(9) for preventing or treating cicatrization disorders or for preventing or for repairing vibices;

(10) for combating disorders of the sebaceous functions, such as acne hyperseborrhoea or simple seborrhoea;

(11) for the treatment or prevention of cancerous or precancerous states;

(12) for the treatment of inflammatory conditions such as arthritis;

(13) for the treatment of any condition of viral origin at the level of the skin or in general;

(14) for the prevention or treatment of alopecia;

(15) for the treatment of dermatological or general conditions including an immunological component;

(16) for the treatment of conditions of the cardiovascular system, such as arteriosclerosis.

For the aforesaid therapeutic or pharmaceutical applications, the compounds according to the invention can advantageously be used in combination with other compounds displaying retinoid-type activity, with the D vitamins or derivatives thereof, with corticosteroids, with anti-free radical agents, with α-hydroxy or α-keto acids or derivatives thereof, or alternatively with ion channel blockers. By "D vitamins or derivatives thereof" are intended, for example, the derivatives of vitamin $D_2$ or $D_3$ and in particular 1,25-dihydroxyvitamin $D_3$. By "anti-free radical agents" are intended, for example, α-tocopherol, superoxide dismutase, ubiquinol or certain metal-chelating agents. By "α-hydroxy or α-keto acids or derivatives thereof" are intended, for example, lactic, malic, citric, glycolic, mandelic, tartaric, glyceric or ascorbic acids or salts, amides or esters thereof. By "ion channel blockers" are intended, for example, minoxidil (2,4-diamino-6-piperidinopyrimidine 3-oxide) and derivatives thereof.

The present invention thus also features medicinal compositions containing at least one compound of formula (I), one of its optical or geometric isomers, or one of its pharmaceutically acceptable salts or other derivatives thereof.

The pharmaceutical/therapeutic compositions of this invention, intended especially for the treatment of the aforesaid disease states comprise a carrier which is pharmaceutically acceptable and compatible with the mode or regime of administration selected for the given composition, at least one compound of formula (I), one of its optical or geometric isomers or one of the salts, etc., thereof.

The administration of the compounds according to the invention can be carried out systemically, enterally, parenterally, topically or ocularly.

For enteral administration, the medicinal/pharmaceutical compositions may be in the form of tablets, gelatin capsules, sugar-coated tablets, syrups, suspensions, solutions, elixirs, powders, granules, emulsions, microopheres or nanospheres or lipid or polymeric vesicles which permit a controlled release. For parenteral administration, the compositions may be in the form of solutions or suspensions for perfusion or for injection.

The compounds according to the invention are generally administered at a daily dose of about 0.01 mg/kg to 100 mg/kg of body weight, and this at the regime or rate of 1 to 3 doses per diem.

For topical administration, the pharmaceutical compositions based on compounds according to the invention are more particularly intended for the treatment of the skin and the mucous membranes and can be provided in the form of ointments, creams, milks, pommades, powders, impregnated pads, solutions, gels, sprays, lotions or suspensions. They may also be provided in the form of microopheres or nanospheres or lipid or polymeric vesicles or polymeric patches and hydrogels which permit a controlled release.

These compositions for topical administration may, moreover, be provided either in anhydrous form or in an aqueous form according to the particular clinical indication.

For ocular administration, they are principally collyria.

These compositions for topical or ocular application contain at least one compound of formula (I), or one of its optical or geometric isomers or, alternatively, one of its salts, etc., at a concentration preferably ranging from 0.001% to 5% by weight relative to the total weight of the composition.

The compounds of formula (I) according to the invention also find application in the cosmetic field, in particular for body and hair care and especially for the treatment of skins with acne tendency, for hair regrowth, against loss, for combating the greasy appearance of the skin or the hair, in the protection against the harmful effects of the sun or in the treatment of physiologically dry skins, for preventing and/or for combating photoinduced or chronologic ageing.

For cosmetic applications, the compositions of the invention may, moreover, be advantageously used in combination with other compounds displaying retinoid-type activity, with the D vitamins or derivatives thereof, with corticosteroids, with anti-free radical agents, with α-hydroxy or α-keto acids or derivatives thereof, or alternatively with ion channel blockers, all of these different active agents being as defined above.

The present invention therefore also features cosmetic compositions comprising a carrier which is cosmetically acceptable and suitable for a topical application, at least one compound of formula (I) or one of its optical or geometric isomers or one of its salts. Such cosmetic compositions are advantageously presented in the form of a cream, a milk, a lotion, a gel, microspheres or nanospheres or lipid or polymeric vesicles, a soap or a shampoo.

The concentration of the compound of formula (I) in the cosmetic compositions according to the invention advantageously ranges from 0.001% to 3% by weight relative to the total composition.

The medicinal and cosmetic compositions according to the invention may, in addition, contain inert or even pharmacodynamically or cosmetically active additives or combinations of these additives, and, especially: wetting agents; depigmenting agents such as hydroquinone, azelaic acid, caffeic acid or kojic acid; emollients; moisturizing agents such as glycerol, PEG 400, thiamorpholinone and its derivatives or alternatively urea; antiseborrhoeic or antiacne agents such as S-carboxymethylcysteine, S-benzylcysteamine, salts or derivatives thereof, benzoyl peroxide; antibiotics such as erythromycin and esters thereof, neomycin, clindamycin and esters thereof, tetracyclines; antifungal agents such as ketoconazole or 4,5-polymethylene-3-isothiazolidones; agents promoting hair regrowth, such as Minoxidil (2,4-diamino-6-piperidinopyrimidine 3-oxide) and derivatives thereof, Diazoxide (7-chloro-3-methyl-1,2,4-benzothiadiazine-1,1-dioxide) and Phenytoin (5,4-diphenyl-2,4-imidazolidinedione); non-steroidal anti-inflammatory agents; carotenoids and especially β-carotene; anti-psoriatic agents such as anthralin and derivatives thereof; and, lastly, 5,8,11,14-eicosatetraynoic and 5,8,11-eicosatrynoic acids and esters and amides thereof.

The compositions according to the invention may also contain taste- or flavor-enhancing agents, preservatives such as parahydroxybenzoic acid esters, stabilizing agents, moisture regulating agents, pH regulating agents, osmotic pressure modifying agents, emulsifying agents, UV-A and UV-B screening agents, antioxidants such as α-tocopherol, butylated hydroxyanisole or butylated hydroxytoluene.

In order to further illustrate the present invention and the advantages thereof, the following specific examples are given, it being understood that same are intended only as illustrative and in nowise limitative.

EXAMPLE 1

Preparation of methyl 4-[3-oxo-3-(5,6,7,8-tetrahydro-5,5,8,8-tetramethyl-2-naphthyl)-1-propynyl]benzoate (a) Preparation of methyl 4-trimethylsilylethynylbenzoate 21.5 g (0.1 mol) of methyl 4-bromobenzoate, 300 ml of triethylamine and a mixture of 200 mg of palladium acetate and of 400 mg of triphenylphosphine were introduced into a three-necked flask under a stream of nitrogen. 20 g (0.204 mol) of trimethylsilylacetylene were then added, the mixture was heated progressively to 90° C. over 1 hour and maintained at this temperature for 5 hours. The reaction mixture was cooled, the salt filtered and evaporated. The residue was taken up with 200 ml of hydrochloric acid (5%) and 400 ml of ethyl ether. The ether phase was separated by settling, washed with water, dried over magnesium sulfate and evaporated. The residue obtained was purified by chromatography on a silica column diluted with dichloromethane. After the evaporation of the solvents, 23 g (100%) of the expected compound were recovered in the form of a colorless oil.

(b) Synthesis of methyl 4-[3-oxo-3-(5,6,7,8-tetrahydro-5,5,8,8-tetramethyl-2-naphthyl)-1-propynyl]benzoate 8.4 g (36 mmol) of 5,6,7,8-tetrahydro-5,5,8,8-tetramethyl-2-naphthoyl chloride, 6.9 g (29.7 mmol) of the above derivative and 100 ml of dichloromethane were introduced into a round-bottomed flask. 16.8 g (125 mmol) of $AlCl_3$ were added at 0° C. in small amounts and stirring was carried out at room temperature for 8 hours. The reaction mixture was poured into ice, extraction was carried out with dichloromethane, and the organic phase was separated by settling, dried over magnesium sulfate and evaporated. The residue obtained was purified by chromatography on a silica column eluted with a mixture of dichloromethane and hexane (50/50). 6.8 g (61%) of the expected compound were recovered, of melting point 113°–114° C.

EXAMPLE 2

Preparation of methyl 4-(3-hydroxy-3-(5,6,7,8-tetrahydro-5,5,8,8-tetramethyl-2-naphthyl)-1-propynyl]benzoate 4.7 g (125 mmol) of the compound obtained in Example 1(b) and 100 ml of methanol were introduced into a round-bottomed flask. 5.7 g (150 mmol) of $CeCl_3.7H_2O$ and 530 mg (125 mmol) of sodium borohydride were added successively while cooling at 0° C. and the mixture was stirred at room temperature for 4 hours. The reaction mixture was poured into a water/ethyl ether mixture and the organic phase was separated by settling, washed with water, dried over magnesium sulfate and evaporated. The residue obtained was triturated in 100 ml of hexane, filtered and dried. 4 g (85%) of the expected compound, with a melting point of 142°–143° C., were recovered.

EXAMPLE 3

Preparation of 4-[3-hydroxy-3-(5,6,7,8-tetrahydro-5,5,8,8-tetramethyl-2-naphthyl)-1-propynyl]benzoic acid 3.5 g (93 mmol) of methyl 4-[3-hydroxy-3-(5,6,7,8-tetrahydro-5,5,8,8-tetramethyl-2-naphthyl)-1-propynyl]benzoate, 200 ml of methanol and 20 ml of a methanolic sodium hydroxide solution (2N) were introduced into a round-bottomed flask. The reaction mixture was stirred at room temperature for 8 hours and evaporated and the residue was taken up in water and acidified with hydrochloric acid. Extraction was carried out with ethyl ether and the organic phase was separated by settling, dried over magnesium sulfate and evaporated. The residue obtained was recrystallized from a cyclohexane/isopropyl ether mixture and 1.7 g (50%) of the expected acid, with a melting point of 134°–135° C., was recovered.

EXAMPLE 4

Preparation of 4-[3-oxo-3-(5,6,7,8-tetrahydro-5,5,8,8-tetramethyl-2-naphthyl)-1-propynyl]benzoic acid 500 mg (1.38 mmol) of 4-(3-hydroxy-3-(5,6,7,8-tetrahydro-5,5,8,8-tetramethyl-2-naphthyl)-1-propynyl]benzoic acid, 50 ml of dichloromethane and 2.4 g (27.6 mmol) of manganese oxide were introduced into a round-bottomed flask which was placed in an ultrasonic bath for 4 hours. The reaction mixture was filtered, the filtrate was evaporated and the residue was purified by simple filtration through silica in ethyl ether. 90 mg (18%) of the expected compound, with a melting point of 208°–209° C., were recovered.

EXAMPLE 5

Preparation of 2-hydroxy-4-[3-oxo-3-(5,6,7,8-tetrahydro-5,5,8,8-tetramethyl-2-naphthyl)-1-propynyl]benzoic acid (a) Preparation of methyl 2-hydroxy-4-trimethylsilylethynylbenzoate Following the basic procedure of Example 1(a), by reacting 34 g (122 mmol) of methyl 2-hydroxy-4-iodobenzoate with 34 ml (244 mmol) of trimethylsilylacetylene, 25.9 g (85%) of the expected compound were obtained in the form of a brown oil.

(b) Preparation of methyl 2-hydroxy-4-[3-oxo-3-(5,6,7,8-tetrahydro-5,5,8,8-tetramethyl-2-naphthyl)-1-propynyl]benzoate Following the basic procedure of Example 1(b), by reacting 2.4 g (0.01 mol) of 5,6,7,8-tetrahydro-5,5,8,8-tetramethyl-2-naphthoyl chloride with 2.5 g (0.01 mol) of methyl 2-hydroxy-4-trimethylsilylethynylbenzoate, 2.9 g (74%) of the expected ester, with a melting point of 189°–190° C., were recovered.

(c) Synthesis of 2-hydroxy-4-[3-oxo-3-(5,6,7,8-tetrahydro-5,5,8,8-tetramethyl-2-naphthyl)-1-propynyl]benzoic acid 1.5 g (3.8 mmol) of the above ester, 100 ml of THF and 485 mg (11.4 mmol) of lithium hydroxide monohydrate were introduced into a round-bottomed flask. The mixture was heated at reflux for 8 hours, was evaporated to dryness and the residue was taken up in water and acidified with hydrochloric acid. Extraction was carried out with ethyl ether and the organic phase was separated by settling, dried over magnesium sulfate and evaporated. The residue obtained was recrystallized from a mixture of cyclohexane and isopropyl ether, filtered and dried. 700 mg (48%) of the expected acid, with a melting point of 183°–184° C., were recovered.

EXAMPLE 6

Preparation of methyl 2-hydroxy-4-[3-hydroxy-3-(5,6,7,8-tetrahydro-5,5,8,8-tetramethyl-2-naphthyl)-1-propynyl]benzoate 2.9 g (7.4 mmol) of methyl 2-hydroxy-4-[3-oxo-3-(5,6,7,8-tetrahydro-5,5,8,8-tetramethyl-2-naphthyl)-1-propynyl]benzoate and 100 ml of a methanol/THF (50/50) mixture were introduced into a round-bottomed flask and 140 mg (3.7 mmol) of sodium borohydride were added in small amounts. The reaction mixture was stirred at room temperature for 2 hours, poured into water and extracted with ethyl ether. The organic phase was separated by settling, dried over magnesium sulfate and evaporated. The residue obtained was purified by chromatography on a silica column eluted with a mixture of dichloromethane and hexane (50/50). After evaporation of the solvents, 1.6 g (55%) of the expected compound, with a melting point of 92°–93° C., was recovered.

EXAMPLE 7

Preparation of 2-hydroxy-4-[3-hydroxy-3-(5,6,7,8-tetrahydro-5,5,8,8-tetramethyl-2-naphthyl)-1-propynyl]benzoic acid Following the basic procedure of Example 6, from 1 g (2.7 mmol) of 2-hydroxy-4-[3-oxo-3-(5,6,7,8-tetrahydro-5,5,8,8-tetramethyl-2-naphthyl)-1-propynyl]benzoic acid, 915 mg (91%) of the expected acid, with a melting point of 203°–204° C. were recovered.

EXAMPLE 8

Preparation of 2-hydroxy-4-[3-oxo-3-(3-tert-butyl-4-methoxyphenyl)-1-propynyl]benzoic acid (a) Preparation of methyl 2-Hydroxy-4-[3-oxo-3-(3-tert-butyl-4-methoxyphenyl)-1-propynyl]benzoate Following the basic procedure of Example 1(b), by reacting 4.2 g (0.02 mol) of 3-tert-butyl-4-methoxybenzoyl chloride with 5 g (0.02 mol) of methyl 2-hydroxy-4-trimethylsilylethynylbenzoate, 6 g (81%) of the expected compound were obtained, after purification by chromatography on a silica column eluted with dichloromethane, in the form of a brown oil.

(b) Synthesis of 2-hydroxy-4-[3-oxo-3-(3-tert-butyl-4-methoxyphenyl)-1-propynyl]benzoic acid Following the basic procedure of Example 5(c), from 6 g (16.4 mmol) of the above compound, 4.2 g (73%) of the expected acid, with a melting point of 204°–205° C., were recovered.

EXAMPLE 9

Preparation of 4-[1-oxo-3-(5,6,7,8-tetrahydro-5,5,8,8-tetramethyl-2-naphthyl)-2-propynyl]benzoic acid (a) Preparation of 5,6,7,8-tetrahydro-5,5,8,8-tetramethyl-2-trimethylsilylethynylnaphthalene Following the basic procedure of Example 1(a), by reacting 26.7 g (0.1 mol) of 2-bromo-5,6,7,8-tetrahydro-5,5,8,8-tetramethylnaphthalene with 20 g (0.204 mol) of trimethylsilylacetylene, 18.8 g (66%) of the expected compound were obtained in the form of a colorless oil.

(b) Preparation of 5,6,7,8-tetrahydro-5,5,8,8-tetramethyl-2-ethynylnaphthalene 5.7 g (0.02 mol) of the above compound and 75 ml of methanol were introduced into a round-bottomed flask and 100 mg of potassium carbonate were added. The reaction mixture was stirred at room temperature for 3 hours, was evaporated to dryness and the residue was taken up in water and ethyl ether. The organic phase was separated by settling, dried over magnesium sulfate and evaporated. 4.1 g (100%) of the expected acetylene were recovered in the form of a yellow oil.

(c) Preparation of allyl 4-(N,N'-dimethylcarbamoyl)benzoate 20 ml of dimethylamine (40% in water) were introduced into a round-bottomed flask and a solution of 2.5 g (11.6 mmol) of 4-(allyloxycarbonyl)benzoyl chloride in 50 ml of THF was added dropwise. The reaction mixture was stirred at room temperature for 1 hour. The reaction mixture was poured into water and extracted with ethyl ether. The organic phase was separated by settling, dried over magnesium sulfate and evaporated. 2.7 g (100%) of the expected amide were recovered in the form of a slightly yellow oil.

(d) Preparation of allyl 4-[1-oxo-3-(5,6,7,8-tetrahydro-5,5,8,8-tetramethyl-2-naphthyl)-2-propynyl]benzoate 4.3 g (20 mmol) of 5,6,7,8-tetrahydro-5,5,8,8-tetramethyl-2-ethynylnaphthalene and 20 ml of THF were introduced into a three-necked flask under a stream of nitrogen. 12.5 ml (20 mmol) of an n-butyllithium solution (1.6M in hexane) were added dropwise at −78° C. and the reaction mixture was stirred for 10 minutes. 2.7 ml of $BF_3$—$Et_2O$ were then added at this same temperature and the reaction mixture was stirred for 30 minutes. A solution of 2.5 g (10 mmol) of allyl 4-(N,N'-dimethylcarbamoyl)benzoate in 10 ml of THF was added, while maintained at −78° C., to the solution and stirring was carried out for 1 hour. The reaction mixture was poured into an aqueous ammonium chloride solution and extraction was carried out with ethyl ether. The organic phase was separated by settling, dried over magnesium sulfate and evaporated. The residue obtained was purified by chromatography on a silica column eluted with a mixture of dichloromethane and hexane (10/90). After evaporation of the solvents, 4.2 g (52%) of the expected ester were recovered in the form of an oil.

(e) Synthesis of 4-[1-oxo-3-(5,6,7,8-tetrahydro-5,5,8,8-tetramethyl-2-naphthyl)-2-propynyl]benzoic acid Following the basic procedure of Example 5(c), from 1.4 g (3.5 mmol) of the above ester, 940 mg (75%) of the expected acid, with a melting point of 191°–192° C., were recovered.

EXAMPLE 10

Preparation of 4-[1-hydroxy-3-(5,6,7,8-tetrahydro-5,5,8,8-tetramethyl-2-naphthyl)-2-propynyl]benzoic acid (a) Preparation of allyl 4-[1-hydroxy-3-[5,6,7,8-tetrahydro-5,5,8,8-tetramethyl-2-naphthyl)-2-propynyl]benzoate Following the basic procedure of Example 6, from 1.7 g (4.2 mmol) of allyl 4-[1-oxo-3-(5,6,7,8-tetrahydro-5,5,8,8-tetramethyl-2-naphthyl)-2-propynyl]benzoate, 1.6 g (94%) of the expected ester were obtained in the form of a colorless oil.

(b) Synthesis of 4-(1-hydroxy-3-(5,6,7,8-tetrahydro-5,5,8,8-tetramethyl-2-naphthyl)-2-propynyl]benzoic acid 950 mg (2.4 mmol) of the above ester, 50 ml of THF and 75 mg of tetrakis(triphenylphosphine)palladium(O) were introduced into a round-bottomed flask under a stream of nitrogen. 2.1 ml (24 mmol) of morpholine were added dropwise at 0° C. and stirring was carried out at ambient temperature for 1 hour. The reaction mixture was evaporated and the residue was taken up in water, acidified to a pH of 1 with hydrochloric acid and extracted with ethyl ether. The organic phase was separated by settling, dried over magnesium sulfate and evaporated. The residue obtained was triturated in a hexane/ethyl ether (80/20) mixture, filtered and dried. 530 mg (62%) of the expected acid, with a melting point of 161°–162° C., were recovered.

EXAMPLE 11

Preparation of methyl-2-hydroxy-4-[3-hydroxy-3-(4,4-dimethylthiochroman-6-yl)-1-propynyl]benzoate (a) Preparation of 4,4-dimethyl-6-thiochromancarboxaldehyde 9.4 g (36.6 mmol) of 4,4-dimethyl-6-bromothiochroman and 100 ml of THF were introduced into a three-necked flask under a stream of nitrogen. 16.1 ml of an n-butyllithium solution (2.5M in hexane) were added dropwise at −78° C. and stirring was carried out for 30 min. 2.7 ml (38.4 mmol) of DMF were then added dropwise and the mixture was permitted to heat to room temperature. The reaction mixture was poured into an aqueous ammonium chloride solution and extracted with ethyl ether. The organic phase was separated by settling, dried over magnesium sulfate and evaporated. The residue obtained was purified by chromatography on a silica column eluted with a mixture of dichloromethane and hexane (50/50). After evaporating the solvents, 6.1 g (81%) of the expected aldehyde were recovered in the form of a yellow oil.

(b) Preparation of α-trimethylsilylethynyl-4,4-dimethyl-6-thiochromanmethanol 3 ml (21.3 mmol) of trimethylsilylacetylene and 50 ml of THF were introduced into a three-necked flask. A solution of 8.6 ml (21.3 mmol) of n-butyllithium (2.5M in hexane) was added dropwise at −78° C. under a stream of nitrogen and the reaction mixture was permitted to heat to room temperature. This solution was introduced dropwise into a solution of 4 g (19.4 mmol) of 4,4-dimethyl-6-thiochromancarboxaldehyde in 50 ml of THF at −78° C. The reaction mixture was permitted to heat to room temperature, was poured into an aqueous ammonium chloride solution and extracted with ethyl ether. The organic phase was separated by settling, dried over magnesium sulfate and evaporated. 5.9 g (100%) of the expected alcohol were obtained in the form of a yellow oil.

(c) Preparation of α-ethynyl-4,4-dimethyl-6-thiochromanmethanol 5.9 g (19.4 mmol) of α-trimethylsilylethynyl-4,4-dimethyl-6-thiochromanmethanol and 50 ml of THF were introduced into a round-bottomed flask and 21.3 ml (23.3 mmol) of a tetrabutylammonium fluoride solution (1.1M in THF) were added dropwise. Stirring was carried out at room temperature for 1 hour and the reaction mixture was poured into water and extracted with ethyl ether. The organic phase was separated by settling, dried over magnesium sulfate and evaporated. The residue obtained was purified by chromatography on a silica column eluted with a mixture of ethyl acetate and hexane (1/4). After evaporating the solvents, 3.9 g (87%) of α-ethylnyl-4,4-dimethyl-6-thiochromanmethanol were recovered in the form of a colorless oil.

(d) Synthesis of methyl 2-hydroxy-4-[3-hydroxy-3-(4,4-dimethylthiochroman-6-yl)-1-propynyl]benzoate 2.5 g (10.8 mmol) of α-ethynyl-4,4-dimethyl-6-thiochromanmethanol, 3 g (10.8 mmol) of methyl 2-hydroxy-4-iodobenzoate and 50 ml of triethylamine were introduced into a three-necked flask. The reaction mixture was degassed with nitrogen for 30 min. and then 600 mg (0.86 mmol) of bis(triphenylphosphine)palladium(II) chloride and 240 mg (1.3 mmol) of copper iodide were added successively. Stirring was carried out at room temperature for four hours, the reaction mixture was evaporated to dryness and the residue obtained was taken up in water and ethyl ether. The organic phase was separated by settling, dried over magnesium sulfate and evaporated. The residue obtained was purified by chromatography on a silica column eluted with dichloromethane. 3.2 g (80%) of methyl 2-hydroxy-4-[3-hydroxy-3-(4,4-dimethylthiochroman-6-yl)-1-propynyl]benzoate, with a melting point of 105°–106° C., were recovered.

EXAMPLE 12

Preparation of 2-hydroxy-4-[3-oxo-3-(4,4-dimethylthiochroman-6-yl)-1-propynyl]benzoic acid (a) Preparation of methyl 2-hydroxy-4-[3-oxo-3-(4,4-dimethylthiochroman-6-yl)-1-propynyl]benzoate 2 g (5.2 mmol) of methyl 2-hydroxy-4-[3-hydroxy-3-(4,4-dimethylthiochroman-6-yl)-1-propynyl]benzoate and 50 ml of dichloromethane were introduced into a round-bottomed flask. 2.6 g (6.9 mmol) of pyridinium dichromate were added and stirring was carried out at room temperature for 8 hours. The reaction mixture was evaporated to dryness and the residue obtained purified by chromatography on a silica column eluted with a mixture of dichloromethane and hexane (50/50). After evaporating the solvents, 1.3 g (65%) of the expected ester was recovered in the form of a brown oil.

(b) Synthesis of 2-hydroxy-4-[3-oxo-3-(4,4-dimethylthiochroman-6-yl)-1-propynyl]benzoic acid 1.3 g (3.42 mmol) of the above ester, 430 mg (10.2 mmol) of lithium hydroxide and 50 ml of THF were introduced into a round-bottomed flask. Heating was carried out at reflux for 8 hours and the reaction mixture was evaporated to dryness. The residue was taken up in water and ethyl ether and acidified. The organic phase was separated by settling, dried over magnesium sulfate and evaporated. The residue obtained was purified by chromatography on a silica column eluted with a mixture of dichloromethane and-methanol (95/5). 600 mg (48%) of the expected acid, with a melting point of 253°–254° C., were recovered.

EXAMPLE 13

Preparation of 4-[3-hydroxy-3-(3-tert-butyl-4-methoxyphenyl)-1-propynyl]benzoic acid (a) Preparation of α-trimethylsilylethynyl-3-tert-butyl-4-methoxybenzenemethanol Following the basic procedure of Example 11(b), by reacting 7.7 g (40 mmol) of 3-tert-butyl-4-methoxybenzaldehyde with one equivalent of lithium trimethylsilylacetylide, 11.1 g (98%) of the expected alcohol were obtained in the form of a colorless oil.

(b) Preparation of α-ethynyl-3-tert-butyl-4-methoxybenzenemethanol

Following the basic procedure of Example 11(c), from 11.1 g (38.2 mmol) of α-trimethylsilylethynyl-3-tert-butyl-4-methoxybenzenemethanol, 8.1 g (96%) of α-ethynyl-3-tert-butyl-4-methoxybenzenemethanol were obtained in the form of a yellow oil.

(c) Preparation of methyl 4-[3-hydroxy-3-(3,tert-butyl-4-methoxyphenyl)-1-propynyl]benzoate Following the basic procedure of Example 11(d), by reacting 2.5 g (11.4 mmol) of α-ethynyl-3-tert-butyl-4-methoxybenzenemethanol with 3.17 g (11.4 mmol) of methyl 2-hydroxy-4-iodobenzoate, 3 g (71%) of the expected ester were obtained in the form of a brown oil.

(d) Synthesis of 4-[3-hydroxy-3-(3-tert-butyl-4-methoxyphenyl)-1-propynyl]benzoic acid Following the basic procedure of Example 12(b), from 4.5 g (12.8 mmol) of methyl 4-[3-hydroxy-3-(3-tert-butyl-4-methoxyphenyl)-1-propynyl]benzoate, 2.45 g (57%) of the expected acid, with a melting point of 114°–115° C., were removed.

EXAMPLE 14

Preparation of methyl N-methyl-4-[3-hydroxy-3-(5,6,7,8-tetrahydro-5,5,8,8-tetramethyl-2-naphthyl)-1-propynyl]-2-pyrrolecarboxylate (a) Preparation of α-trimethylsilylethynyl-5,6,7,8-tetrahydro-5,5,8,8-tetramethyl-2-naphthalenemethanol 17.13 ml (0.121 mol) of trimethylsilylacetylene and 100 ml of THF were introduced into a three-necked flask. A solution of 48.5 ml (0.121 mol) of n-butyllithium (2.5M in hexane) was added dropwise at −78° C. under a stream of nitrogen and the mixture was permitted to heat to room temperature. This solution was introduced dropwise into a solution of 23.8 g (0.11 mol) of 5,6,7,8-tetrahydro-5,5,8,8-tetramethyl-2-naphthalenecarboxaldehyde in 100 ml of THF at −78° C. The reaction mixture was permitted to heat to room temperature, was poured into an aqueous ammonium chloride solution and was extracted with ethyl ether. The organic phase was separated by settling, dried over magnesium sulfate and evaporated. The residue obtained was purified by chromatography on a silica column eluted with a mixture of dichloromethane and hexane (50/50). After evaporating the solvents, 29.9 g (86%) of the expected alcohol were recovered in the form of a yellow oil.

(b) Preparation of α-ethynyl-5,6,7,8-tetrahydro-5,5,8,8-tetramethyl-2-naphthalenemethanol 29.9 g (92.5 mmol) of α-trimethylsilylethynyl-5,6,7,8-tetrahydro-5,5,8,8-tetramethyl-2-naphthalenemethanol and 100 ml of THF were introduced into a round-bottomed flask and 103.8 ml (114.2 mmol) of a tetrabutylammonium fluoride solution (1.1M in THF) were added dropwise. Stirring was carried out at room temperature for one hour and the reaction mixture was poured into water and extracted with ethyl ether. The organic phase was separated by settling, dried over magnesium sulfate and evaporated. The residue obtained was purified by chromatography on a silica column eluted with a mixture of ethyl acetate and hexane (1/4). After evaporating the solvents, 18.1 g (79%) of α-ethynyl-5,6,7,8-tetrahydro-5,5,8,8-tetramethyl-2-naphthalenemethanol, with a melting point of 56°–57° C., were recovered.

(c) Preparation of 2-trichloroacetylpyrrole 45 g (247 mmol) of trichloroacetyl chloride and 100 ml of ethyl ether were introduced into a three-necked flask. A solution of 15.4 g (230 mmol) of pyrrole in 100 ml of ethyl ether was added dropwise and stirring was carried out at room temperature for one hour. A solution of 20 g of potassium carbonate in 60 ml of water was then slowly added. The organic phase was separated by settling, dried over magnesium sulfate and evaporated and the residue was triturated in hexane and filtered. 42.7 g (87%) of the expected compound, with a melting point of 78°–79° C., were recovered.

(d) Preparation of 4-iodo-2-trichloroacetylpyrrole 8.4 g (39.5 mmol) of 2-trichloroacetylpyrrole and 100 ml of chloroform were introduced into a three-necked flask under a stream of nitrogen and 8.6 g (39.5 mmol) of silver trifluoroacetate and 10.16 g (39.5 mmol) of iodine were added successively. Stirring was carried out at room temperature for one hour and the reaction mixture was poured into ice and extracted with dichloromethane. The organic phase was separated by settling, dried over magnesium sulfate and evaporated. The residue obtained was triturated in hexane and filtered. 8.2 g (61%) of the expected compound, with a melting point of 118°–119° C., were recovered.

(e) Preparation of methyl 4-iodo-2-pyrrolecarboxylate 8.2 g (24 mmol) of 4-iodo-2-trichloroacetylpyrrole and 100 ml of methanol were introduced into a round-bottomed flask and 2 g (36 mmol) of sodium methoxide were added. Stirring was carried out at room temperature for four hours, the reaction mixture was evaporated to dryness and the residue obtained was taken up in water and ethyl ether. The organic phase was separated by settling, dried over magnesium sulfate and evaporated. The residue obtained was triturated in heptane and filtered. 4.9 g (81%) of the expected ester, with a melting point of 77°–78° C., were recovered.

(f) Preparation of methyl N-methyl-4-iodo-2-pyrrolecarboxylate 780 mg (25.9 mmol) of sodium hydride (80% in oil) and 20 ml of DMF were introduced into a three-necked flask, a solution of 6.5 g (25.9 mmol) of methyl 4-iodo-2-pyrrolecarboxylate in 50 ml of DMF was added dropwise and stirring was carried out until gas evolution has ceased. 2.1 ml (33.6 mmol) of iodomethane were then added and stirring was carried out at room temperature for two hours. The reaction mixture was poured into water and extracted with ethyl ether. The organic phase was separated by settling, dried over magnesium sulfate and was evaporated. The residue obtained was purified by chromatography on a silica column eluted with a mixture of dichloromethane and hexane (40/60). 4.5 g (65%) of methyl N-methyl-4-iodo-2-pyrrolecarboxylate, with a melting point of 64°–65° C., were recovered.

(g) Synthesis of methyl N-methyl-4-[3-hydroxy-3-(5,6,7,8-tetrahydro-5,5,8,8-tetramethyl-2-naphthyl)-1-propynyl]-2-pyrrolecarboxylate Following the basic procedure of Example 11(d), by reacting 2.9 g (12 mmol) of α-ethynyl-5,6,7,8-tetrahydro-5,5,8,8-tetramethyl-2-naphthalenemethanol with 3.2 g (12.1 mmol) of methyl N-methyl-4-iodo-2-pyrrolecarboxylate, 2.8 g (61%) of the expected ester, with a melting point of 150°–152° C., were recovered by trituration in isopropyl ether.

EXAMPLE 15

Preparation of N-methyl-4-[3-hydroxy-3-(5,6,7,8-tetrahydro-5,5,8,8-tetramethyl-2-naphthyl)-1-propynyl]-2-pyrrolecarboxylic acid Following the basic procedure of Example 12(b), from 2 g (5.2 mmol) of methyl N-methyl-4-[3-hydroxy-3-(5,6,7,8-tetrahydro-5,5,8,8-tetramethyl-2-naphthyl)-1-propynyl]-2-pyrrolecarboxylate, 440 mg (22%) of the expected acid, with a melting point of 112°–113° C., were recovered.

EXAMPLE 16

Preparation of methyl 4-[3-hydroxy-3-(5,6,7,8-tetrahydro-5,5,8,8-tetramethyl-2-naphthyl)-1-propynyl]-2-pyrrolecarboxylate

(a) Preparation of methyl N-tert-butoxycarbonyl-4-iodo-2-pyrrolecarboxylate 780 mg (25.9 mmol) of sodium hydride (80% in oil) and 20 ml of DMF were introduced into a three-necked flask, a solution of 6.5 g (25.9 mmol) of methyl 4-iodo-2-pyrrolyecarboxylate in 50 ml of DMF was added dropwise and stirring was carried out until gas evolution has ceased. 5.6 g (25.9 mmol) of di-tert-butyl dicarbonate were then added in small amounts and stirring was carried out at room temperature for two hours. The reaction mixture was poured into water and extracted with ethyl ether. The organic phase was separated by settling, dried over magnesium sulfate and evaporated. The residue obtained was purified by chromatography on a silica column eluted with a mixture of dichloromethane and hexane (60/40). 6.8 g (75%) of methyl N-tert-butoxycarbonyl-4-iodo-2-pyrrolecarboxylate were recovered in the form of a yellow oil.

(b) Preparation of methyl N-tert-butoxycarbonyl-4-[3-hydroxy-3-(5,6,7,8-tetrahydro-5,5,8,8-tetramethyl-2-naphthyl)-1-propynyl]-2-pyrrolecarboxylate:

Following the basic procedure of Example 11(d), by reacting 2 g (8.2 mmol) of α-ethynyl-5,6,7,8-tetrahydro-5,5,8,8-tetramethyl-2-naphthalenemethanol with 3 g (8.5 mmol) of methyl N-tert-butoxycarbonyl-4-iodo-2-pyrrolecarboxylate, 3.8 g (98%) of the expected ester were obtained in the form of a brown oil.

(c) Synthesis of methyl 4-[3-hydroxy-3-(5,6,7,8-tetrahydro-5,5,8,8-tetramethyl-2-naphthyl)-1-propynyl]-2-pyrrolecarboxylate:

2.4 g (5.1 mmol) of the above ester, 20 ml of THF and 20 ml of methanol were introduced into a round-bottomed flask. 278 mg (5.1 mmol) of sodium methoxide were added and stirring was carried out at room temperature for four hours. The reaction mixture was evaporated to dryness and the residue was taken up in water and ethyl ether. The organic phase was separated by settling, dried over magnesium sulfate and evaporated. The residue obtained was triturated in a mixture of diisopropyl ether and heptane and filtered. 1.22 g (65%) of the expected ester, with a melting point of 95°–100° C., was recovered.

EXAMPLE 17

Preparation of methyl 2-hydroxy-4-[3-hydroxy-3-(4,4-dimethylthiochroman-7-yl)-1-propynyl]benzoate:

(a) Preparation of 4,4-dimethyl-7-thiochromancarboxaldehyde:

Following the basic procedure of Example 11(a), from 5.6 g (21.8 mmol) of 4,4-dimethyl-7-bromothiochroman, 3.3 g (74%) of the expected aldehyde were obtained in the form of a yellow oil.

(b) Preparation of α-trimethylsilylethynyl-4,4-dimethyl-7-thiochromanmethanol:

Following the basic procedure of Example 11(b), from 5.4 g (26.2 mmol) of 4,4-dimethyl-7-thiochromancarboxaldehyde, 8 g (100%) of α-trimethylsilylethynyl-4,4-dimethyl-7-thiochromanmethanol were obtained in the form of a yellow oil.

(c) Preparation of α-ethynyl-4,4-dimethyl-7-thiochromanmethanol:

Following the basic procedure of Example 11(c), from 8 g (26.3 mmol) of α-trimethylsilylethynyl-4,4-dimethyl-7-thiochromaranethanol, 4.3 g (70%) of the expected alcohol, after purification, were obtained in the form of a colorless oil.

(d) Synthesis of methyl 2-hydroxy-4-(3-hydroxy-3-(4,4-dimethylthiochroman-7-yl)-1-propynyl]benzoate:

2.5 g (10.8 mmol) of α-ethynyl-4,4-dimethyl-7-thiochromanmethanol, 3 g (10.8 mmol) of methyl 2-hydroxy-4-iodobenzoate and 50 ml of triethylamine were introduced into a three-necked flask. The reaction mixture was degassed with nitrogen for 30 min. and then 600 mg (0.86 mmol) of bis(triphenylphosphine)palladium(II) chloride and 240 mg (1.3 mmol) of copper iodide were successively added. Stirring was carried out at room temperature for four hours and the reaction mixture was evaporated to dryness and the residue obtained taken up in water and ethyl ether. The organic phase was separated by settling, dried over magnesium sulfate and evaporated. The residue obtained was purified by chromatography on a silica column eluted with dichloromethane. 3.2 g (80%) of methyl 2-hydroxy-4-[3-hydroxy-3-(4,4-dimethylthiochroman-7-yl)-1-propynyl]benzoate, with a melting point of 101°–102° C., were recovered.

EXAMPLE 18

Preparation of 4-[1-hydroxy-3-(4,4-dimethylthiochroman-6-yl)-2-propynyl]benzoic acid:

(a) Preparation of 2,2-dibromo-1-(4,4-dimethylthiochroman-6-yl)ethylene:

5 g (24.2 mmol) of 4,4-dimethyl-6-thiochromancarboxaldehyde, prepared in Example 11(a), and 50 ml of dichloromethane were introduced into a round-bottomed flask. 16.1 g (48.4 mmol) of carbon tetrabromide, 12.7 g (48.4 mmol) of triphenylphosphine and 3.16 g (48.4 mmol) of zinc powder were successively added and stirring was carried out at room temperature for two hours. The reaction mixture was evaporated and the residue obtained purified by chromatography on a silica column eluted with hexane. 7.75 g (88%) of the expected compound were recovered.

(b) Preparation of (4,4-dimethylthiochroman-6-yl)acetylene:

7.7 g (21.2 mmol) of 2,2-dibromo-1-(4,4-dimethylthiochroman-6-yl) ethylene and 80 ml of THF were introduced into a three-necked flask under a stream of nitrogen. 17 ml (26.6 mmol) of an n-butyllithium solution (2.5M in hexane) were added dropwise at −78° C. and the mixture was permitted to heat to room temperature for one hour. The reaction mixture was poured into water and extracted with ethyl ether. The organic phase was separated by settling, dried over magnesium sulfate and evaporated. The residue obtained was purified by chromatography on a silica column eluted with heptane. 3.9 g (90%) of the expected acetylene derivative were recovered in the form of a yellow oil.

(c) Synthesis of 4-[1-hydroxy-3-(4,4-dimethylthiochroman-6-yl)-2-propynyl]benzoic acid:

2 g (9.9 mmol) of (4,4-dimethylthiochroman-6-yl) acetylene and 25 ml of THF were introduced into a three-necked flask under a stream of nitrogen, 4 ml (9.9 mmol) of an n-butyllithium solution (2.5M in hexane) were added dropwise at −50° C. and stirring was carried out for 30 min. A solution of 743 mg (4.9 mmol) of 4-carboxybenzaldehyde in 25 ml of THF was then added and stirring was carried out at room temperature for one hour. The reaction mixture was poured into water and extracted with ethyl ether. The organic phase was separated by settling, dried over magnesium sulfate and evaporated. The residue was recrystallized from diisopropyl ether. After filtration, 730 mg (42%) of the expected acid, with a melting point of 168°–169° C., were obtained.

EXAMPLE 19

Preparation of 2-hydroxy-4-[3-hydroxy-3-(4,4-dimethylthiochroman-6-yl)-1-propynyl]benzoic acid:

Following the basic procedure of Example 12(b), from 2 g (5.2 mmol) of methyl 2-hydroxy-4-[3-hydroxy-3-(4,4-dimethylthiochroman-6-yl)-1-propynyl]benzoate, 1.66 g (86%) of the expected acid, with a melting point of 240°–245° C., was obtained.

EXAMPLE 20

Preparation of 2-hydroxy-4-[3-hydroxy-3-(4,4-dimethylthiochroman-7-yl)-1-propynyl]benzoic acid:

Following the basic procedure of Example 12(b), from 2 g (5.2 mmol) of methyl 2-hydroxy-4-[3-hydroxy-3-(4,4-dimethylthiochroman-7-yl)-1-propynyl]benzoate, 1.55 g (80%) of the expected acid, with a melting point of 144°–145° C., was obtained.

EXAMPLE 21

Preparation of (+)-isomer of methyl 4-[3-hydroxy-3-(5,6,7,8-tetrahydro-5,5,8,8-tetramethyl-2-naphthyl)-1-propynyl]benzoate:

(a) Preparation of (−)-diastereoisomer of 1-(5,6,7,8-tetrahydro-5,5,8,8-tetramethyl-2-naphthyl)-2-propynyl (R)-α-methoxyphenylacetate:

9.7 g (40 mmol) of α-ethynyl-5,6,7,8-tetramethyl-2-naphthalenemethanol, 6.7 g (40 mmol) of (R)-(−)-α-methoxyphenylacetic acid and 100 ml of dichloromethane were introduced into a round-bottomed flask. 8.3 g (40 mmol) of dicyclohexylcarbodiimide and 4.9 g (40 mmol) of 4-dimethylaminopyridine were successively added and stirring was carried out at room temperature for 24 hours. The reaction mixture was poured into water and extracted with ethyl ether. The organic phase was separated by settling, dried over magnesium sulfate and evaporated. The residue obtained was purified by chromatography on a silica column eluted with a mixture of dichloromethane and heptane (60/40). After evaporating the solvents, 3.8 g (97%) of the mixture of diastereoisomers were recovered the form of an oil.

Separation of the two diastereoisomers was carried out by two successive recrystallizations from isooctane. 6 g (38.4%) of the (−)-diastereoisomer, with a melting point of 94°–95° C., were thus obtained.

$[\alpha]_D^{20}$=−14°8 (c=1, $CH_2Cl_2$)

(b) Preparation of (−)-isomer of α-ethynyl-5,6,7,8-tetrahydro-5,5,8,8-tetramethyl-2-naphthalenemethanol:

5.7 g (14.6 mmol) of the (−)-diastereoisomer prepared above and 20 ml of THF were introduced into a round-bottomed flask and 10 ml of a methanolic sodium hydroxide solution (2N) were added. Stirring was carried out at room temperature for one hour and the reaction mixture was evaporated to dryness and taken up in water and ethyl ether. The organic phase was separated by settling, dried over magnesium sulfate and evaporated. The residue obtained was purified by chromatography on a silica column eluted with dichloromethane. After evaporating the solvents, 3.4 g (97%) of the (−)-isomer of α-ethynyl-5,6,7,8-tetrahydro-5,5,8,8-tetramethyl-2-naphthalenemethanol, with a melting point of 77°–78° C., were recovered.

$[\alpha]_D^{20}$ =−20°7 (c=1, $CH_2Cl_2$)

(c) Synthesis of (+)-isomer of methyl 4-(3-hydroxy-3-(5,6,7,8-tetrahydro-5,5,8,8-tetramethyl-2-naphthyl)-1-propynyl]benzoate:

Following the basic procedure of Example 11(d), by reacting 1.6 g (6.6 mmol) of the (−)-isomer of α-ethynyl- 5,6,7,8-tyetrahydro-5,5,8,8-tetramethyl-2-naphthalenemethanol with 1.7 g (6.6 mmol) of methyl 4-iodobenzoate, there were obtained, after chromatography on a silica column eluted with a mixture of dichloromethane and heptane (60/40), 2.1 g (84.6%) of the (+)-isomer of methyl 4-[3-hydroxy-3-(5,6,7,8-tetrahydro-5,5,8,8-tetramethyl-2-naphthyl)-1-propynyl]benzoate, with a melting point of 128°–129° C.

$[\alpha]_D^{20}$=+18°6 (c=1, $CH_2Cl_2$)

EXAMPLE 22

Preparation of (−)-isomer of 4-[3-hydroxy-3-(5,6,7,8-tetrahydro-5,5,8,8-tetramethyl-2-naphthyl)-1-propynyl]benzoic acid:

Following the basic procedure of Example 12(b), from 1.6 g of the (+)-isomer of methyl 4-[3-hydroxy-3-(5,6,7,8-tetrahydro-5,5,8,8-tetramethyl-2-naphthyl)-1-propynyl]benzoate, 1.1 g (73%) of the (−)-isomer of 4-[3-hydroxy-3-(5,6,7,8-tetrahydro-5,5,8,8-tetramethyl-2-naphthyl)-1-propynyl]benzoic acid, with a melting point of 183°–184° C., was obtained.

$[\alpha]_D^{20}$=−1.1° (c=1, DMF)

EXAMPLE 23

Preparation of (+)-isomer of methyl 2-hydroxy-4-[3-hydroxy-3-(5,6,7,8-tetrahydro-5,5,8,8-tetramethyl-2-naphthyl)-1-propynyl]benzoate:

Following the basic procedure of Example 11(d), by reacting 1.5 g (6.2 mmol) of the (−)-isomer of α-ethynyl-5,6,7,8-tetrahydro-5,5,8,8-tetramethyl-2-naphthalenemethanol with 1.7 g (6.2 mmol) of methyl 2-hydroxy-4-iodobenzoate, there were obtained, after chromatography on a silica column eluted with a mixture of dichloromethane and heptane (70/30), 2.2 g (91%) of the (+)-isomer of methyl 2-hydroxy-4-(3-hydroxy-3-(5,6,7,8-tetrahydro-5,5,8,8-tetramethyl-2-naphthyl)-1-propynyl]benzoate, with a melting point of 100°–101° C.

$[\alpha]_D^{20}$=+17°9 (c=1, $CH_2Cl_2$)

EXAMPLE 24

Preparation of (−)-isomer of 2-hydroxy-4-[3-hydroxy-3-(5,6,7,8-tetrahydro-5,5,8,8-tetramethyl-2-naphthyl)-1-propynyl]benzoic acid:

Following the basic procedure of Example 12(b), from 1.8 g of the (+)-isomer of methyl 2-hydroxy-4-(3-hydroxy-3-(5,6,7,8-tetrahydro-5,5,8,8-tetramethyl-2-naphthyl)-1-propynyl]benzoate, 1.5 g (88%) of the (−)-isomer of 2-hydroxy-4-[3-hydroxy-3-(5,6,7,8-tetrahydro-5,5,8,8-tetramethyl-2-naphthyl)-1-propynyl]benzoic acid, with a melting point of 220° C. with decomposition, was obtained.

$[\alpha]_D^{20}$=−1° (c=1, DMF)

EXAMPLE 25

Preparation of (−)-isomer of methyl 4-[3-hydroxy-3-(5,6,7,8-tetrahydro-5,5,8,8-tetramethyl-2-naphthyl)-1-propynyl]benzoate:

(a) Preparation of (+)-diastereoisomer of 1-(5,6,7,8-tetrahydro-5,5,8,8-tetramethyl-2-naphthyl)-2-propynyl (S)-α-methoxyphenylacetate:

9.3 g (38.4 mmol) of α-ethynyl-5,6,7,8-tetrahydro-5,5,8,8-tetramethyl-2-naphthalenemethanol, 6.4 g (38.4 mmol) of (S)-(+)-α-methoxyphenylacetic acid and 100 ml of dichloromethane were introduced into a round-bottomed flask. 7.9 g (38.4 mmol) of dicyclohexylcarbodiimide and 4.7 g (38.4 mmol) of 4-dimethylaminopyridine were successively added and stirring was carried out at room temperature for 24 hours. The reaction mixture was poured into water and extracted with ethyl ether. The organic phase was separated by settling, dried over magnesium sulfate and evaporated. The residue obtained was purified by chromatography on a silica column eluted with a mixture of dichloromethane and heptane (60/409). After evaporating the solvents, 12.5 (84%) of the mixture of diastereoisomers were recovered in the form of an oil. Separation of the two diastereoisomers was carried out by two successive recrystallizations from isooctane. 4 g (27%) of the (+)-diastereoisomer, with a melting point of 93°–94° C., were thus obtained.

$[\alpha]_D^{20}$=+16°9 (c=1, $CH_2Cl_2$)

(b) Preparation of (+)-isomer of α-ethynyl-5,6,7,8-tetrahydro-5,5,8,8-tetramethyl-2-naphthalenemethanol:

3.7 g (9.5 mmol) of the (+)-diastereoisomer prepared above and 20 ml of THF were introduced into a round-bottomed flask and 10 ml of a methanolic sodium hydroxide solution (2N) were added. Stirring was carried out at room temperature for one hour and the reaction mixture was evaporated to dryness and taken up in water and ethyl ether. The organic phase was separated by settling, dried over magnesium sulfate and evaporated. The residue obtained was purified by chromatography on a silica column eluted with dichloromethane. After evaporating the solvents, 1 g (87%) of the (+)-isomer of α-ethynyl-5,6,7,8-tetrahydro-5,5,8,8-tetramethyl-2-naphthalenemethanol, with a melting point of 77°–78° C., was recovered.

$[\alpha]_D^{20}$=+18°7 (c=1, $CH_2Cl_2$)

(c) Synthesis of (−)-isomer of methyl 4-(3-hydroxy-3-(5,6,7,8-tetrahydro-5,5,8,8-tetramethyl-2-naphthyl)-1-propynyl]benzoate:

Following the basic procedure of Example 11(d), by reacting 700 mg (2.9 mmol) of the (+)-isomer of α-ethynyl-5,6,7,8-tetrahydro-5,5,8,8-tetramethyl-2-naphthalenemethanol with 760 mg (2.9 mmol) of methyl 4-iodobenzoate, there was obtained, after chromatography on a silica column eluted with a mixture of dichloromethane and heptane (60/40), 1 g (92.5%) of the (−)-isomer of methyl 4-[3-hydroxy-3-(5,6,7,8-tetrahydro-5,5,8,8-tetramethyl-2-naphthyl)-1-propynyl]benzoate, with a melting point of 128°–129° C.

$[\alpha]_D^{20}$=−18°1 (c=1, $CH_2Cl_2$)

EXAMPLE 26

Preparation of (−)-isomer of methyl 2-hydroxy-4-(3-hydroxy-3-(5,6,7,8-tetrahydro-5,5,8,8-tetramethyl-2-naphthyl)-1-propynyl]benzoate:

Following the basic procedure of Example 121(d), by reacting 1 g (4.1 mmol) of the (+)-isomer of α-ethynyl-5,6,7,8-tetrahydro-5,5,8,8-tetramethyl-2-naphthalenemethanol with 1.1 g (4.1 mmol) of methyl 2-hydroxy-4-iodobenzoate, there was obtained, after chromatography on a silica column eluted with a mixture of dichloromethane and heptane (70/30), 1.45 g (90%) of the (−)-isomer of methyl 2-hydroxy-4-(3-hydroxy-3-(5,6,7,8- tetrahydro-5,5,8,8-tetramethyl-2-naphthyl)-1-propynyl] benzoate, with a melting point of 100°–101° C.

$[\alpha]_D^{20} = -17°6$ (c=1, CH$_2$Cl$_2$)

EXAMPLE 27

Preparation of (+)-isomer of 4-[3-hydroxy-3-(5,6,7,8-tetrahydro-5,5,8,8-tetramethyl-2-naphthyl)-1-propynyl]benzoic acid:

Following the basic procedure of Example 12(b), from 800 mg of the (−)-isomer of methyl 4-[3-hydroxy-3-(5,6,7,8-tetrahydro-5,5,8,8-tetramethyl-2-naphthyl)-1-propynyl] benzoate, 600 mg (78%) of the (+)-isomer of 4-[3-hydroxy-3-(5,6,7,8-tetrahydro-5,5,8,8-tetramethyl-2-naphthyl)-1-propynyl]benzoic acid, with a melting point of 180°–181° C., were obtained.

$[\alpha]_D^{20} = +1.1°$ (c=1, DMF)

EXAMPLE 28

Preparation of (+)-isomer of 2-hydroxy-4-[3-hydroxy-3-(5,6,7,8-tetrahydro-5,5,8,8-tetramethyl-2-naphthyl)-1-propynyl]benzoic acid:

Following the basic procedure of Example 12(b), from 1.2 g of the (−)-isomer of methyl 2-hydroxy-4-(3-hydroxy-3-(5,6,7,8-tetrahydro-5,5,8,8-tetramethyl-2-naphthyl)-1-propynyl]benzoate, 1 g (87%) of the (+)-isomer of 2-hydroxy-4-(3-hydroxy-3-(5,6,7,8-tetrahydro-5,5,8,8-tetramethyl-2-naphthyl)-1-propynyl]benzoic acid, with a melting point of 220° C. with decomposition, was obtained.

$[\alpha]_D^{20} = +1°$ (c=1, DMF)

EXAMPLE 29

Preparation of methyl 2-hydroxy-4-[3-hydroxy-3-methyl-3-(5,6,7,8-tetrahydro-5,5,8,8-tetramethyl-2-naphthyl)-1-propynyl]benzoate:

(a) Preparation of 1-trimethylsilylethynyl-1-(5,6,7,8-tetrahydro-5,5,8,8-tetramethyl-2-naphthyl) ethanol:

Following the basic procedure of Example 11(b), by reacting 5 g (21.7 mmol) of 2-acetyl-5,6,7,8-tetrahydro-5,5,8,8-tetramethylnaphthalene with one equivalent of lithium trimethyl silylacetylide, 6.8 g (95%) of the expected alcohol were obtained in the form of a colorless oil.

(b) Preparation of 1-ethynyl-1-(5,6,7,8-tetrahydro-5,5,8,8-tetramethyl-2-naphthyl) ethanol:

Following the basic procedure of Example 11(c), from 6.8 g (20.7 mmol) of 1-trimethylsilylethynyl-1-(5,6,7,8-tetrahydro-5,5,8,8-tetramethyl-2-naphthyl) ethanol, 4.22 g (75%) of the expected compound, with a melting point of 84°–85° C., were obtained.

(c) Synthesis of methyl 2-hydroxy-4-[3-hydroxy-3-methyl-3-(5,6,7,8-tetrahydro-5,5,8,8-tetramethyl-2-naphthyl)-1-propynyl]benzoate:

Following the basic procedure of Example 11(d), by reacting 2 g (7.8 mmol) of 1-ethynyl-1-(5,6,7,8-tetrahydro-5,5,8,8-tetramethyl-2-naphthyl) ethanol with 2.2 g (7.9 mmol) of methyl 2-hydroxy-4-iodobenzoate, there were obtained, after chromatography on a silica column eluted with a mixture of dichloromethane and heptane (50/50), 2.77 g (87%) of the expected ester, with a melting point of 110°–115° C.

EXAMPLE 30

Preparation of 2-hydroxy-4-[3-hydroxy-3-methyl-3-(5,6,7,8-tetrahydro-5,5,8,8-tetramethyl-2-naphthyl)-1-propynyl]benzoic acid:

Following the basic procedure of Example 12(b), from 2.2 g (5.4 mmol) of methyl 2-hydroxy-4-[3-hydroxy-3-methyl-3-(5,6,7,8-tetrahydro-5,5,8,8-tetramethyl-2-naphthyl)-1propynyl]benzoate, 1.9 g (89%) of the expected acid, with a melting point of 265°–270° C., was obtained.

EXAMPLE 31

Preparation of 2-Methoxy-4-[3-hydroxy-3-(5,6,7,8-tetrahydro-5,5,8,8-tetramethyl-2-naphthyl)-1-propynyl]benzoic acid:

(a) Preparation of methyl 4-iodo-2-methoxybenzoate:

238 mg (7.9 mmol) of sodium hydride (80% in oil) and 20 ml of DMF were introduced into a three-necked flask, a solution of 2 g (7.2 mmol) of methyl 2-hydroxy-4-iodobenzoate in 50 ml of DMF was added dropwise and stirring was carried out until gas evolution had ceased. 540 μl (8.6 mmol) of iodomethane were then added and stirring was carried out at room temperature for two hours. The reaction mixture was poured into water and extracted with ethyl ether. The organic phase was separated by settling, dried over magnesium sulfate and evaporated. 2.1 g (100%) of methyl 4-iodo-2-methoxybenzoate were recovered.

(b) Preparation of methyl 2-methoxy-4-[3-hydroxy-3-(5,6,7,8-tetrahydro-5,5,8,8-tetramethyl-2-naphthyl)-1-propynyl]benzoate:

Following the basic procedure of Example 11(d), by reacting 1.66 g (6.8 mmol) of α-ethynyl-5,6,7,8-tetrahydro-5,5,8,8-tetramethyl-2-naphthalenemethanol with 2 g (6.9 mmol) of methyl 4-iodo-2-methoxybenzoate, 2.1 g (75%) of the expected ester were obtained, after chromatography on a silica column eluted with dichloromethane, in the form of a yellow oil.

(c) Synthesis of 2-methoxy-4-[3-hydroxy-3-(5,6,7,8-tetrahydro-5,5,8,8-tetramethyl-2-naphthyl)-1-propynyl]benzoic acid:

Following the basic procedure of Example 12(b), from 2.1 g (5.2 mmol) of the above ester, 1 g (50%) of the expected acid, with a melting point of 100°–102° C., was obtained.

EXAMPLE 32

Preparation of 4-[3-hydroxy-3-(5,6,7,8-tetrahydro-5,5,8,8-tetramethyl-2-naphthyl)-1-propynyl] benzaldehyde:

2.42 g (10 mmol) of α-ethynyl-5,6,7,8-tetrahydro-5,5,8,8-tetramethyl-2-naphthalenemethanol, 2 g (11 mmol) of 4-bromobenzaldehyde and 50 ml of triethylamine were introduced into a three-necked flask. The reaction mixture was degassed with nitrogen for 30 min. and then 169 mg (0.75 mmol) of palladium(II) acetate and 393 mg (1.5 mmol) of triphenylphosphine were successively added. Heating was carried out at 60° C. for one hour, the reaction mixture was evaporated to dryness and the residue obtained was taken up in water and ethyl ether. The organic phase was separated by settling, dried over magnesium sulfate and evaporated. The residue obtained was purified by chromatography on a silica column eluted with a mixture of dichloromethane and heptane (70/30). 1.23 g (35.5%) of 4-(3-hydroxy-3-(5,6,7,8-tetrahydro-5,5,8,8-tetramethyl-2-naphthyl)-1-propynyl]benzaldehyde, with a melting point of 104°–105° C., was recovered.

EXAMPLE 33

Preparation of 4-[3-hydroxy-3-(5,6,7,8-tetrahydro-5,5,8,8-tetramethyl-2-naphthyl)-1-propynyl]benzyl acetate:

Following the basic procedure of Example 32, by reacting 2.42 g (10 mmol) of α-ethynyl-5,6,7,8-tetrahydro-5,5,8,8-tetramethyl-2-naphthalenemethanol with 2.52 g (11 mmol) of 4-bromobenzyl acetate, 790 mg (20%) of the expected compound were obtained in the form of a brown oil.

EXAMPLE 34

Preparation of 4-[3-hydroxy-3-(5,6,7,8-tetrahydro-5,5,8,8-tetramethyl-2-naphthyl)-1-propynyl] benzenemethanol:

780 mg (2 mmol) of 4-[3-hydroxy-3-(5,6,7,8-tetrahydro-5,5,8,8-tetramethyl-2-naphthyl)-1-propynyl]benzyl acetate and 30 ml of THF were introduced into a round-bottomed flask. 5 ml of a 2N methanolic sodium hydroxide solution were added and stirring was carried out for 30 min. The reaction mixture was poured into water and extracted with ethyl ether. The organic phase was separated by settling, dried over magnesium sulfate and evaporated. The residue obtained was triturated in heptane and filtered, 419 mg (60%) of the expected compound, with a melting point of 85°–86° C., were recovered.

EXAMPLE 35

Preparation of 4-[3-hydroxy-3-(5,6,7,8-tetrahydro-5,5,8,8-tetramethyl-2-naphthyl)-1-propynyl]toluene:

Following the basic procedure of Example 11(d), by reacting 1.2 g (5 mmol) of α-ethynyl-5,6,7,8-tetrahydro-5,5,8,8-tetramethyl-2-naphthalenemethanol with 1.1 g (5 mmol) of 4-iodotoluene, 1.49 g (45%) of the expected compound was recovered, after chromatography on a silica column eluted with dichloromethane, in the form of a brown oil.

EXAMPLE 36

Preparation of 4-[3-hydroxy-3-(5,6,7,8-tetrahydro-3,5,5,8,8-pentamethyl-2-naphthyl)-1-propynyl]phenyl acetate:

(a) Preparation of 2-bromo-5,6,7,8-tetrahydro-3,5,5,8,8-pentamethylnaphthalene:

30 ml of 2-bromotoluene and 14 g (0.11 mol) of AlCl$_3$ were introduced into a three-necked flask, cooling was carried out to 0° C. and a solution of 50 g (0.27 mol) of 2,5-dichloro-2,5-dimethylhexane in 100 ml of 2-bromotoluene was added dropwise, and the reaction mixture was permitted to heat to room temperature. The reaction mixture was poured into water and extracted with dichloromethane. The organic phase was separated by settling, washed with an aqueous sodium bicarbonate solution and evaporated. The product crystallized on stirring in methanol. After filtration, 56.9 g (75%) of 2-bromo-5,6,7,8-tetrahydro-3,5,5,8,8-pentamethylnaphthalene, with a melting-point of 92°–93° C., were recovered.

(b) Preparation of 5,6,7,8-tetrahydro-3,5,5,8,8-pentamethyl-2-naphthalenecarboxaldehyde:

Following the basic procedure of Example 11(a), from 8.44 g (30 mmol) of 2-bromo-5,6,7,8-tetrahydro-3,5,5,8,8-pentamethylnaphthalene, 6.9 g (100%) of this expected aldehyde, with a melting point of 75°–76° C., were obtained.

(c) Preparation of α-trimethylsilylethynyl-5,6,7,8-tetrahydro-3,5,5,8,8-pentamethyl-2-naphthalenemethanol:

Following the basic procedure of Example 11(*b*), by reacting 6.66 g (29 mmol) of 5,6,7,8-tetrahydro-3,5,5,8,-pentamethyl-2-naphthalenecarboxaldehyde with one equivalent of lithium trimethylsilylactylide, 8.8 g (92%) of the expected alcohol, with a melting point of 95°–96° C., were obtained.

(d) Preparation of α-ethynyl-5,6,7,8-tetrahydro-3,5,5,8,8-pentamethyl-2-naphthalenemethanol:

Following the basic procedure of Example 11(c), from 8.6 g (26 mmol) of α-trimethylsilylethynyl-5,6,7,8-tetrahydro-3,5,5,8,8-pentamethyl-2-naphthalenemethanol, 4.8 g (72%) of the expected compound, with a melting point of 101°–102° C., were obtained.

(e) Synthesis of 4-[3-hydroxy-3-(5,6,7,8-tetrahydro-3,5,5,8,8-pentamethyl-2-naphthyl)-1-propynyl] phenyl acetate:

Following the basic procedure of Example 11(d), by reacting 1.28 g (5 mmol) of α-ethynyl-5,6,7,8-tetrahydro-3,5,5,8,8-pentamethyl-2-naphthalenemethanol with 1.44 g (5.5 mmol) of 4-iodophenyl acetate, 480 mg (25%) of the expected compound, with a melting point of 129°–130° C., were obtained.

EXAMPLE 37

Preparation of 4-[3-hydroxy-3-(5,6,7,8-tetrahydro-3,5,5,8,8-pentamethyl-2-naphthyl)-1-propyl]phenol:

Following the basic procedure of Example 34, from 300 mg (0.77 mmol) of 4-[3-hydroxy-3-(5,6,7,8-tetrahydro-3,5,5,8,8-pentamethyl-2-naphthyl)-1-propynyl]phenyl acetate, 207 mg (77%) of 4-[3-hydroxy-3-(5,6,7,8-tetrahydro-3,5,5,8,8-pentamethyl-2-naphthyl)-1-propynyl]phenol, with a melting point of 158°–159° C., were obtained.

EXAMPLE 38

Preparation of 4-[3-hydroxy-3-(5,6,7,8-tetrahydro-5,5,8,8-tetramethyl-2-naphthyl)-1-propynyl] phenylsulfinylmethane:

(a) Preparation of 4-bromophenylsulfinylmethane:

4.06 g (20 mmol) of 4-bromothioanisole and 75 ml of dichloromethane were introduced into a round-bottomed flask and 6.3 g (20 mmol) of meta-chloroperbenzoic acid were added. Stirring was carried out at room temperature for four hours and the reaction mixture was poured into water. The organic phase was separated by settling, dried over magnesium sulfate and evaporated. The residue obtained was purified by chromatography on a silica column eluted with a mixture of dichloromethane and heptane (70/30).

After evaporating the solvents, 1.22 g (28%) of the expected sulfoxide, with a melting point of 80°–81° C., was recovered.

(b) Synthesis of 4-(3-hydroxy-3-(5,6,7,8-tetrahydro-5,5,8,8-tetramethyl-2-naphthyl)-1-propynyl)phenylsulfinylmethane:

Following the basic procedure of Example 32, by reacting 1.21 g (5 mmol) of αethynyl-5,6,7,8-tetrahydro-5,5,8,8-tetramethyl-2-naphthalenemethanol with 1.1 g (5 mmol) of 4-bromophenylsulfinylmethane, 177 mg (9%) of the expected sulfoxide compound, with a melting point of 121°–122° C., were obtained.

EXAMPLE 39

Preparation of 4-[3-hydroxy-3-(5,6,7,8-tetrahydro-5,5,8,8-tetramethyl-2-naphthyl)-1-propynyl]phenylsulfinylmethane (a) Preparation of 4-bromophenylsulfonylmethane:

Following the basic procedure of Example 38(a), by reacting 2.03 g (10 mmol) of 4-bromothioanisole with 10.35 g (30 mmol) of metachloroperbenzoic acid, 1.72 g (73%) of the expected sulfone, with a melting point of 94°–95° C., was obtained.

(b) Synthesis of 4-[3-hydroxy-3-(5,6,7,8-tetrahydro-5,5,8,8-tetramethyl-2-naphthyl)-1-propynyl]phenylsulfonylmethane:

Following the basic procedure of Example 32, by reacting 1.21 g (5 mmol) of α-ethynyl-5,6,7,8-tetrahydro-5,5,8,8-tetramethyl-2-naphthalenemethanol with 1.18 g (5 mmol) of 4-bromophenylsulfonylmethane, 610 mg (31%) of the expected sulfone compound, with a melting point of 112°–113° C., were obtained.

EXAMPLE 40

Preparation of N-ethyl-4-[3-hydroxy-3-(5,6,7,8-tetrahydro-5,5,8,8-tetramethyl-2-naphthyl)-1-propynyl]benzamide:

(a) Preparation of 4-iodobenzoyl chloride:

5 g (20 mmol) of 4-iodobenzoic acid, 30 ml of toluene and 5 drops of DMF were introduced into a round-bottomed flask. Heating was carried out to 40° C., 1.74 ml (24 mmol) of thionyl chloride was added and stirring was carried out for 30 minutes. Evaporation was carried out to dryness and 5.5 g (100%) of the crude acid chloride were recovered, which compound was employed as is in the continuation of the synthesis.

(b) Preparation of N-ethyl-4-iodobenzamide:

90 ml (45 mmol) of a 0.5N solution of ethylamine in THF were introduced into a round-bottomed flask and a solution of 4 g (15 mmol) of 4-iodobenzoyl chloride in 20 ml of dichloromethane was added dropwise. Stirring was carried out at room temperature for one hour and the reaction mixture was poured into water and extracted with ethyl ether. The organic phase was separated by settling, dried over magnesium sulfate and evaporated. The residue obtained was purified by chromatography on a silica column eluted with dichloromethane. After evaporating the solvents, 3.41 g (82%) of the expected amide was recovered.

(c) Synthesis of N-ethyl-4-(3-hydroxy-(5,6,7,8-tetrahydro-5,5,8,8-tetramethyl-2-naphthyl)-1-propynyl]benzamide:

Following the basic procedure of Example 11(d), by reacting 1.21 g (5 mmol) of α-ethynyl-5,6,7,8-tetrahydro-5,5,8,8-tetramethyl-2-naphthalenemethanol with 1.37 g (5.1 mmol) of N-ethyl-4-iodobenzamide, 596 mg (31%) of the expected amide, with a melting point of 153°–154° C., were obtained.

EXAMPLE 41

Preparation of N,N'-diethyl-4-[3-hydroxy-3-(5,6,7,8-tetrahydro-5,5,8,8-tetramethyl-2-naphthyl)-1-propynyl]benzamide:

(a) Preparation of N,N'-diethyl-4-iodobenzamide:

Following the basic procedure of Example 40(b), by reacting 5 g (18 mmol) of 4-iodobenzoyl chloride with 5.6 ml (54 mmol) of diethylamine, 3.4 g (62%) of the expected amide were obtained.

(b) Synthesis of N,N'-diethyl-4-[3-hydroxy-3-(5,6,7,8-tetrahydro-5,5,8,8-tetramethyl-2-naphthyl)-1-propynyl)benzamide:

Following the basic procedure of Example 11(d), by reacting 970 mg (4 mmol) of α-ethynyl-5,6,7,8-tetrahydro-5,5,8,8-tetramethyl-2-naphthalenemethanol with 1.25 g (4.1 mmol) of N,N'-diethyl-4-iodobenzamide, 584 mg (35%) of the expected amide were obtained in the form of a brown oil.

EXAMPLE 42

Preparation of morpholide of 4-[3-hydroxy-3-(5,6,7,8-tetrahydro-5,5,8,8-tetramethyl-2-naphthyl)-1-propynyl]benzoic acid:

(a) Preparation of morpholide of 4-iodobenzoic acid:

Following the basic procedure of Example 40(b), by reacting 4 g (15 mmol) of 4-iodobenzoyl chloride with 3.9 ml (45 mmol) of morpholine, 3.64 g (76%) of the expected amide were obtained.

(b) Synthesis of morpholide of 4-(3-hydroxy-3-(5,6,7,8-tetrahydro-5,5,8,8-tetramethyl-2-naphthyl)-1-propynyl]benzoic acid Following the basic procedure of Example 11(d), by reacting 1.21 g (5 mmol) of α-ethynyl-5,6,7,8-tetrahydro-5,5,8,8-tetramethyl-2-naphthalenemethanol with 1.62 g (5.1 mmol) of the morpholide of 4-iodobenzoic acid, 423 mg (20%) of the expected amide, with a melting point of 122°–123° C., were obtained.

EXAMPLE 43

Preparation of methyl 5-[3-hydroxy-3-[5,6,7,8-tetrahydro-5,5,8,8-tetramethyl-2-naphthyl)-1-propynyl]-2-thiophenecarboxylate:

Following the basic procedure of Example 32 by reacting 1.21 g (5 mmol) of α-ethynyl-5,6,7,8-tetrahydro-5,5,8,8-tetramethyl-2-naphthalenemethanol with 1.1 g (5 mmol) of methyl 5-bromo-2-thiophenecarboxylate, 371 mg (19%) of the expected methyl ester, with a melting point of 84°–85° C., were obtained.

EXAMPLE 44

Preparation of methyl 2-hydroxy-4-[3-hydroxy-3-(5,6,7,8-tetrahydro-3,5,5,8,8-pentamethyl-2-naphthyl)-1-propynyl]benzoate:

Following the basic procedure of Example 11(d), by reacting 1.28 g (5 mmol) of α-ethynyl-5,6,7,8-tetrahydro-3,5,5,8,8-pentamethyl-2-naphthalenemethanol [prepared in Example 37(d)] with 1.5 g (5.5 mmol) of methyl 2-hydroxy-4-iodobenzoate, 739 mg (36%) of the expected compound, with a melting point of 112°–113° C., were obtained.

EXAMPLE 45

Preparation of 2-hydroxy-4-[3-hydroxy-3-(5,6,7,8-tetrahydro-3,5,5,8,8-pentamethyl-2-naphthyl)-1-propynyl]benzoic acid:

Following the basic procedure of Example 12(b), from 600 mg (1.5 mmol) of methyl 2-hydroxy-4-(3-hydroxy-3-(5,6,7,8-tetrahydro-3,5,5,8,8-pentamethyl-2-naphthyl)-1-propynyl]benzoate, 132 mg (23%) of the expected acid, with a melting point of 88°–89° C., were obtained.

EXAMPLE 46

Preparation of methyl 2-hydroxy-4-[3-hydroxy-3-(3-methoxy-5,6,7,8-tetrahydro-5,5,8,8-tetramethyl-2-naphthyl)-1-propynyl]benzoate:

(a) Preparation of 2-bromo-3-hydroxy-5,6,7,8-tetrahydro-5,5,8,8-tetramethylnaphthalene:

36.6 g (0.2 mol) of 2,5-dichloro-2,5-dimethylhexane, 34.6 g (0.2 mol) of 2-bromophenol and 400 ml of dichloromethane were introduced successively into a three-necked flask. 26.6 g (0.2 mol) of $AlCl_3$ were added in small amounts at 0° C. and stirring was carried out until gas evolution had ceased (violent reaction). The reaction mixture was poured into water and the organic phase was separated by settling, washed with an aqueous sodium bicarbonate solution, dried over magnesium sulfate and evaporated. The residue was purified by chromatography on a silica column eluted with a mixture of ethyl acetate and heptane (10/90). After evaporating the solvents, 20.6 g (36%) of the expected phenol were recovered.

(b) Preparation of 2-bromo-3-methoxy-5,6,7,8-tetrahydro-5,5,8,8-tetramethylnaphthalene:

720 mg (24 mmol) of sodium hydride (80% in oil) and 20 ml of DMF were introduced into a three-necked flask, a solution of 5.7 g (20 mmol) of 2-bromo-3-hydroxy-5,6,7,8-tetrahydro-5,5,8,8-tetramethylnaphthalene in 75 ml of DMF was added dropwise and stirring was carried out until gas evolution had ceased. 1.5 ml (24 mmol) of iodomethane was then added and stirring was carried out at room temperature for two hours. The reaction mixture was poured into water and extracted with ethyl ether. The organic phase was separated by settling, dried over magnesium sulfate and evaporated. The residue obtained was triturated in heptane and filtered. 5.5 g (93%) of 2-bromo-3-methoxy-5,6,7,8-tetrahydro-5,5,8,8-tetramethylnaphthalene, with a melting point of 70°–71° C., were recovered.

(c) Preparation of 3-methoxy-5,6,7,8-tetrahydro-5,5,8,8-tetramethyl-2-naphthalenecarboxaldehyde:

Following the basic procedure of Example 11(a), from 5.3 g (17.8 mmol) of 2-bromo-3-methoxy-5,6,7,8-tetrahydro-5,5,8,8-tetramethylnaphthalene, 3.5 g (80%) of the expected aldehyde, with a melting point of 125°–126° C., were obtained.

(d) Preparation of α-trimethylsilylethynyl-3-methoxy-5,6,7,8-tetrahydro-5,5,8,8-tetramethyl-2-naphthalenemethanol:

Following the basic procedure of Example 11(b), by reacting 3.21 g (13 mmol) of 3-methoxy-5,6,7,8-tetrahydro-5,5,8,8-tetramethyl-2-naphthalenecarboxaldehyde with one equivalent of lithium trimethylsilylacetylide, 4.4 g (99%) of the expected alcohol were obtained in the form of a yellow oil.

(e) Preparation of α-ethynyl-3-methoxy-5,6,7,8-tetrahydro-5,5,8,8-tetramethyl-2-naphthalenemethanol:

Following the basic procedure of Example 11(c), from 4.4 g (12.7 mmol) of α-trimethylsilylethynyl-3-methoxy-5,6,7,8-tetrahydro- 5,5,8,8-tetramethyl-2-naphthalenemethanol, 1.15 g (33%) of the expected compound was obtained.

(f) Synthesis of methyl 2-hydroxy-4-[3-hydroxy-3-(3-methoxy-5,6,7,8-tetrahydro-5,5,8,8-tetramethyl-2-naphthyl)-1-propynyl]benzoate:

Following the basic procedure of Example 11(d), by reacting 1.15 g (4.2 mmol) of α-ethynyl-3-methoxy-5,6,7,8-tetrahydro-5,5,8,8-tetramethyl-2-naphthalenemethanol with 1.21 g (4.64 mmol) of methyl 2-hydroxy-4-iodobenzoate, 1.36 g (76%) of the expected product, with a melting point of 125°–126° C., were obtained.

EXAMPLE 47

Preparation of 2-hydroxy-4-[3-hydroxy-3-(3-methoxy-5,6,7,8-tetrahydro-5,5,8,8-tetramethyl-2-naphthyl)-1-propynyl]benzoic acid:

Following the basic procedure of Example 12(g), from 1.1 g (2.6 mmol) of methyl 2-hydroxy-4-[3-hydroxy-3-(3-methoxy-5,6,7,8-tetrahydro-5,5,8,8-tetramethyl-2-naphthyl)-1-propynyl]benzoate, 890 mg (84%) of the expected acid, with a melting point of 225°–228° C., were obtained.

EXAMPLE 48

Preparation of 4-[3-hydroxy-3-(4,4-dimethylthiochroman-6-yl)-1-propynyl]benzoic acid:

(a) Preparation of methyl 4-[3-Hydroxy-3-(4,4-dimethylthiochroman-6-yl)-1-propynyl]benzoate:

Following the basic procedure of Example 11(d), by reacting 1.4 g (6 mmol) of α-ethynyl-4,4-dimethyl-6-thiochromanmethanol with 1.6 g (6 mmol) of methyl 4-iodobenzoate, 1.5 g (68%) of the expected ester was obtained in the form of an orange-colored oil.

(b) Synthesis of 4-[3-hydroxy-3-(4,4-dimethylthiochroman-6-yl)-1-propynyl]benzoic acid:

Following the basic procedure of Example 12(b), from 1 g (2.7 mmol) of methyl 4-[3-hydroxy-3-(4,4-dimethylthiochroman-6-yl)-1-propynyl]benzoate, 450 mg (47%) of the expected acid, with a melting point of 147°–149° C., were obtained.

EXAMPLE 49

Preparation of 4-[3-hydroxy-3-(4,4-dimethylthiochroman-7-yl)-1-propynyl]benzoic acid:

(a) Preparation of methyl 4-[3-Hydroxy-3-(4,4-dimethylthiochroman-7-yl)-1-propynyl]benzoate:

Following the basic procedure of Example 11(d), by reacting 2 g (8.6 mmol) of α-ethynyl-4,4-dimethyl-7-thiochromanmethanol with 2.25 g (8.6 mmol) of methyl 4-iodobenzoate, 1.8 g (57%) of the expected ester was obtained in the form of an yellow oil.

(b) Synthesis of 4-[3-hydroxy-3-(4,4-dimethylthiochroman-7-yl)-1-propynyl]benzoic acid:

Following the basic procedure of Example 12(b), from 1.2 g (3.3 mmol) of methyl 4-[3-Hydroxy-3-(4,4-dimethylthiochroman-7-yl)-1-propynyl]benzoate, 300 mg (26%) of the expected acid, with a melting point of 151°–153° C., were obtained.

EXAMPLE 50

Preparation of methyl 3-methyl-4-[3-hydroxy-3-(5,6,7,8-tetrahydro-5,5,8,8-tetramethyl-2-naphthyl)-1-propynyl]benzoate:

(a) Preparation of 3-methyl-4-iodobenzoic acid:

20 g (0.132 mol) of 3-methyl-4-aminobenzoic acid and 175 ml of sulfuric acid (20%) were introduced into a three-necked flask. A solution of 11.9 g (0.172 mol) of sodium nitrite in 50 ml of water was added dropwise at −10° C. and stirring was carried out for two hours. This solution was introduced dropwise via a refrigerated dropping funnel at −50° C. into a solution of 35 g (0.211 mol) of potassium iodide, 35.2 g (0.185 mol) of copper iodide and 175 ml of sulfuric acid (20%). Stirring was carried out for eight hours, the reaction mixture was filtered and the solid obtained was dissolved in ethyl acetate. Washing was carried out with water and then with a sodium sulfite solution, drying was carried out over magnesium sulfate and evaporation was carried out. 24.4 g (70%) of 3-methyl-4-iodobenzoic acid, with a melting point of 205°–210° C., were recovered.

(b) Preparation of methyl 3-methyl-4-iodobenzoate:

24.4 g (0.093 mol) of 3-methyl-4-iodobenzoic acid and 250 ml of methanol were introduced into a round-bottomed flask and 2.5 ml of concentrated sulfuric acid were added dropwise. Heating was carried out at reflux for twelve hours, the reaction mixture was evaporated and the residue taken up in ethyl acetate and water. The organic phase was separated by settling, dried over magnesium sulfate and evaporated. The residue was triturated in methanol and filtered. 21.9 g (85%) of the expected methyl ester, with a melting point of 58°–59° C., were recovered.

(c) Synthesis of methyl 3-methyl-4-[3-hydroxy-3-(5,6,7,8-tetrahydro-5,5,8,8-tetramethyl-2-naphthyl)-1-propynyl]benzoate:

Following the basic procedure of Example 11(d), by reacting 2.4 g (10 mmol) of α-ethynyl-5,6,7,8-tetrahydro-5,5,8,8-tetramethyl-2-naphthalenemethanol with 2.7 g (10 mmol) of methyl 3-methyl-4-iodobenzoate, 3.2 g (83%) of the expected ester, with a melting point of 130°–131° C., were obtained.

EXAMPLE 51

Preparation of 3-Methyl-4-[3-hydroxy-3-(5,6,7,8-tetrahydro-5,5,8,8-tetramethyl-2-naphthyl)-1-propynyl]benzoic acid:

Following the basic procedure of Example 12(d), from 2.2 g (5.6 mmol) of methyl 3-methyl-4-(3-hydroxy-3-(5,6,7,8-tetrahydro-5,5,8,8-tetramethyl-2-naphthyl)-1-propynyl]benzoate, 1.5 g (71%) of 3-methyl-4-(3-hydroxy-3-(5,6,7,8-tetrahydro-5,5,8,8-tetramethyl-2-naphthyl)-1-propynyl]benzoic acid, with a melting point of 189°–190° C., was obtained.

EXAMPLE 52

Preparation of 2-chloro-4-[3-hydroxy-3-(5,6,7,8-tetrahydro-5,5,8,8-tetramethyl-2-naphthyl)-1-propynyl]benzoic acid:

(a) Preparation of 2-chloro-4-iodobenzoic acid:

Following the basic procedure of Example 50(a), from 10 g (58.3 mmol) of 2-chloro-4-aminobenzoic acid, 14.26 g (86%) of 2-chloro-4-iodobenzoic acid were recovered.

(b) Preparation of methyl 2-chloro-4-iodobenzoate:

Following the basic procedure of Example 50(b), from 13.9 g (49.2 mmol) of 2-chloro-4-iodobenzoic acid, 11.52 g (79%) of the expected methyl ester were obtained in the form of an oil.

(c) Preparation of methyl 2-chloro-4-(3-hydroxy-3-(5,6,7,8-tetrahydro-5,5,8,8-tetramethyl-2-naphthyl)-1-propynyl)benzoate:

Following the basic procedure of Example 11(d), by reacting 1.2 g (5 mmol) of α-ethynyl-5,6,7,8-tetrahydro-5,5,8,8-tetramethyl-2-naphthalenemethanol with 1.6 g (5 mmol) of methyl 2-chloro-4-iodobenzoate, 1.7 g (83%) of the expected ester was obtained in the form of a brown oil.

(d) Synthesis of 2-chloro-4-[3-hydroxy-3-[5,6,7,8-tetrahydro-5,5,8,8-tetramethyl-2-naphthyl)-1-propynyl]benzoic acid:

Following the basic procedure of Example 12(b), from 1.7 g (4.1 mmol) of methyl 2-chloro-4-[3-hydroxy-3-(5,6,7,8-tetrahydro-5,5,8,8-tetramethyl-2-naphthyl)-1-propynyl]benzoate, 730 mg (44%) of 2-chloro-4-[3-hydroxy-3-(5,6,7,8-tetrahydro-5,5,8,8-tetramethyl-2-naphthyl)-1-propynyl]benzoic acid, with a melting point of 145°–148° C., were obtained.

EXAMPLE 53

Preparation of 2-acetoxy-4-[3-acetoxy-3-(5,6,7,8-tetrahydro-5,5,8,8-tetramethyl-2-naphthyl)-1-propynyl]benzoic acid:

500 mg (1.3 mmol) of 2-hydroxy-4-(3-hydroxy-3-(5,6,7,8-tetrahydro-5,5,8,8-tetramethyl-2-naphthyl)-1-propynyl] benzoic acid and 10 ml of pyridine were introduced into a round-bottomed flask and 150 ul (1.56 mmol) of acetic anhydride were added dropwise. Stirring was carried out at room temperature for 2 hours, the reaction mixture was evaporated to dryness and the residue was taken up in water and acidified to a pH of 4. Extraction was carried out with ethyl ether, drying was carried out over magnesium sulfate and evaporation was carried out. The residue obtained was purified by chromatography on a silica column eluted with ethyl ether. 230 mg (39%) of 2-acetoxy-4(3-acetoxy-3-(5,6,7,8-tetrahydro-5,5,8,8-tetramethyl-2-naphthyl)-1-propynyl]benzoic acid, with a melting point of 113°–115° C., were recovered.

EXAMPLE 54

Preparation of methyl 4-[3-hydroxy-3-(3-tert-butyl-4-propyloxyphenyl)-1-propynyl]benzoate:

(a) Preparation of 3-tert-butyl-4-propyloxybromobenzene:

Following the basic procedure of Example 46(a), by reacting 4.58 g (0.02 mol) of 3-tert-butyl-4-hydroxybromobenzene with 2.2 ml (0.022 mol) of 1-iodopropane, 4.7 g (87%) of 3-tert-butyl-4-propyloxybromobenzene were obtained in form of a colorless oil.

(b) Preparation of 3-tert-butyl-4-propyloxybenzaldehyde:

Following the basic procedure of Example 11(a), from 4.5 g (16.6 mmol) of 3-tert-butyl-4-propyloxybromobenzene, 3.65 g (100%) of the expected aldehyde were obtained in the from of slightly yellow oil.

(c) Preparation of α-trimethylsilylethynyl-3-tert-butyl-4-(propyloxy)benzenemethanol:

Following the basic procedure of Example 11(b), by reacting 3.6 g (16.4 mmol) of 3-tert-butyl-4-propyloxybenzaldehyde with one equivalent of lithium trimethylsilylacetylide, 5.2 g (100%) of the expected alcohol were obtained in the from of a colorless oil.

(d) Preparation of α-ethynyl-3-tert-butyl-4-(propyloxy)benzenemethanol:

Following the basic procedure of Example 11(c), from 5.1 g (14.1 mmol) of α-trimethylsilyethynyl-3-tert-butyl-4-(propyloxy)benzenemethanol, there were obtained, after chromatography on a silica column eluted with a mixture of dichloromethane and heptane (60/40), 3.3 g (80%) of α-ethynyl-3-tert-butyl-4-(propyloxy)benzenemethanol in the form of a yellow oil.

(e) Synthesis of methyl 4-[3-hydroxy-3-(3-tert-butyl-4-propyloxyphenyl)-1-propynyl]benzoate:

Following the basic procedure of Example 11(d), by reacting 3.3 g (13.4 mmol) of α-ethynyl-3-tert-butyl-4-(propyloxy)benzenemethanol with 3.8 g (13.4 mmol) of methyl 2-hydroxy-4-iodobenzoate, 4.4 g (83%) of methyl 4-[3-hydroxy-3-(3-tert-butyl-4-propyloxyphenyl)-1-propynyl]benzoate were obtained in the form of a dark brown oil.

EXAMPLE 55

Preparation of methyl 4-[3-hydroxy-3-(3-tert-butyl-4-hexyloxyphenyl)-1-propynyl]benzoate:

(a) Preparation of 3-tert-butyl-4-hexyloxybromobenzene:

Following the basic procedure of Example 46(a), by reacting 4.58 g (0.02 mol) of 3-tert-butyl-4-hydroxybromobenzene with 3.3 ml (0.022 mol) of 1-iodohexane, 6 g (97%) of 3-tert-butyl-4-hexyloxybromobenzene were obtained in the from of a colorless oil.

(b) Preparation of 3-tert-butyl-4-hexyloxybenzaldehyde:

Following the basic procedure of Example 11(a), from 5.9 g (18.8 mmol) of 3-tert-butyl-4-hexyloxybromobenzene, 4.9 g (100%) of the expected aldehyde were obtained in the from of a slightly yellow oil.

(c) Preparation of α-trimethylsilylethynyl-3-tert-butyl-4-(hexyloxy)benzenemethanol:

Following the basic procedure of Example 11(b), by reacting 4.8 g (18.3 mmol) of 3-tert-butyl-4-hexyloxybenzaldehyde with one equivalent of lithium trimethylsilylacetylide, 6.6 g (100%) of the expected alcohol were obtained in the from of a colorless oil.

(d) Preparation of α-ethynyl-3-tert-butyl-4-(hexyloxy)benzenemethanol:

Following the basic procedure of Example 11(c), from 6.6 g (18.3 mmol) of α-trimethylsilylethynyl-3-tert-butyl-4-(hexyloxy)benzenemethanol, there were obtained, after chromatography on a silica column eluted with a mixture of dichloromethane and heptane (60/40), 4.3 g (81%) of α-ethynyl-3-tert-butyl-4-(hexyloxy)benzenemethanol in the form of a yellow oil.

(e) Synthesis of methyl 4-[3-hydroxy-3-(3-tert-butyl-4-hexyloxyphenyl)-1-propynyl]benzoate:

Following the basic procedure of Example 11(d), by reacting 3.8 g (13.2 mmol) of α-ethynyl-3-tert-butyl-4-(hexyloxy)benzenemethanol with 3.7 g (13.7 mmol) of methyl 2-hydroxy-4-iodobenzoate, 4 g (69%) of methyl 4-[3-hydroxy-3-(3-tert-butyl-4-hexyloxyphenyl)-1-propynyl]benzoate were obtained in the form of a dark brown oil.

EXAMPLE 56

In this example, various specific formulations based on the compounds according to the invention are illustrated.

| | | |
|---|---|---|
| (A) ORAL ROUTE | | |
| (a) 0.2 g Tablet | | |
| (i) | Compound prepared in Example 7 | 0.001 g |
| (ii) | Starch | 0.114 g |
| (iii) | Dicalcium phosphate | 0.020 g |
| (iv) | Silica | 0.020 g |
| (v) | Lactose | 0.030 g |
| (vi) | Talc | 0.010 g |
| (vii) | Magnesium stearate | 0.005 g |
| (b) Oral suspension in 5 ml ampoules | | |
| (i) | Compound prepared in Example 3 | 0.001 g |
| (ii) | Glycerin | 0.500 g |
| (iii) | Sorbitol at 70% | 0.500 g |
| (iv) | Sodium saccharinate | 0.010 g |
| (v) | Methyl parahydroxybenzoate | 0.040 g |
| (vi) | Flavoring | qs |
| (vii) | Purified water qs | 5 ml |
| (c) 0.8 g Tablet | | |
| (i) | Compound of Example 6 | 0.500 g |
| (ii) | Pregelatinized starch | 0.100 g |
| (iii) | Microcrystalline cellulose | 0.115 g |
| (iv) | Lactose | 0.075 g |
| (v) | Magnesium stearate | 0.010 g |

| | | |
|---|---|---|
| (d) | Oral suspension in 10 ml ampoules | |
| (i) | Compound of Example 2 | 0.200 g |
| (ii) | Glycerin | 1.000 g |
| (iii) | Sorbitol at 70% | 1.000 g |
| (iv) | Sodium saccharinate | 0.010 g |
| (v) | Methyl parahydroxybenzoate | 0.080 g |
| (vi) | Flavoring | qs |
| (vii) | Purified water qs | 10 ml |
| (B) | TOPICAL ROUTE | |
| (a) | Ointment | |
| (i) | Compound of Example 9 | 0.020 g |
| (ii) | Isopropyl myristate | 81.700 g |
| (iii) | Fluid paraffin oil | 9.100 g |
| (iv) | Silica ("Aerosil 200", marketed by DEGUSSA) | 9.180 g |
| (b) | Ointment | |
| (i) | Compound of Example 10 | 0.300 g |
| (ii) | Petroleum jelly | 100 g |
| (c) | Nonionic water-in-oil cream | |
| (i) | 2-Hydroxy-4-[3-hydroxy-3-(3-tert-butyl-4-hydroxyphenyl)-1-propynyl]benzoic acid | 0.100 g |
| (ii) | Mixture of emulsive lanolin alcohols, waxes and oils ("anhydrous Eucerin" marketed by BDF) | 39.900 g |
| (iii) | Methyl parahydroxybenzoate | 0.075 g |
| (iv) | Propyl parahydroxybenzoate | 0.075 g |
| (v) | Sterile demineralized water qs | 100 g |
| (d) | Lotion | |
| (i) | Compound of Example 8 | 0.100 g |
| (ii) | Polyethylene glycol (PEG 400) | 69.900 g |
| (iii) | Ethanol at 95% | 30.000 g |
| (e) | Hydrophobic ointment | |
| (i) | Compound of Example 7 | 0.300 g |
| (ii) | Isopropyl myristate | 36.400 g |
| (iii) | Silicone oil ("Rhodorsil 47 V 300" marketed by RHONE-POULENC) | 36.400 g |
| (iv) | Beeswax | 13.600 g |
| (v) | Silicone oil ("Abil 300.000 cst" marketed by GOLDSCHMIDT) | 100 g |
| (f) | Nonionic oil-in-water cream | |
| (i) | Compound of Example 3 | 1.000 g |
| (ii) | Cetyl alcohol | 4.000 g |
| (iii) | Glycerol monostearate | 2.500 g |
| (iv) | PEG 50 stearate | 2.500 g |
| (v) | Shea butter | 9.200 g |
| (vi) | Propylene glycol | 2.000 g |
| (vii) | Methyl parahydroxybenzoate | 0.075 g |
| (viii) | Propyl parahydroxybenzoate | 0.075 g |
| (ix) | Sterile demineralized water | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalent thereof.

What is claimed is:

1. A method for treating a keratinization disorder, a dermatological disorder, an ophthalmological disorder, skin aging, epidermal and/or dermal atrophy, a cicatrization disorder, a sebaceous function disorder, a cancerous or precancerous disease state, inflammation, a viral infection, alopecia, a cardiovascular disorder, an immune deficiency, a rheumatic disorder, or a respiratory disorder, in a mammalian organism in need of such treatment, comprising administering to such organism a therapeutically effective amount of a pharmaceutical composition of matter which comprises a therapeutically effective amount of a polyaromatic propynyl compound or a pharmaceutically acceptable salt or isomer thereof, wherein the polyaromatic propynyl compound has the structural formula (I):

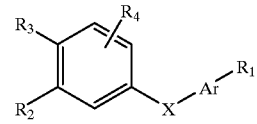

(I)

in which X is one of the radicals:

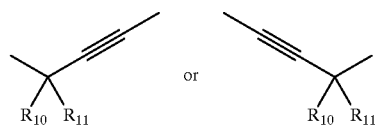

Ar is a radical of the following formula (a):

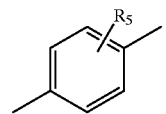

(a)

$R_1$ is (i) a hydrogen atom, (ii) a radical —$CH_3$, (iii) a radical —$CH_2$—O—$R_6$, (iv) a radical —O—$R_6$, (v) a radical —CO—$R_7$, or (vi) a radical —S(O)$_t R_9$; $R_2$ and $R_3$ form, with the carbon atoms from which they depend, a 5- or 6-membered ring optionally substituted by methyl groups and/or optionally interrupted by an oxygen or sulfur atom; $R_4$ is a hydrogen atom, a halogen atom, a lower alkyl radical or a radical —$OR_6$; $R_5$ has the definition of $R_4$, and $R_4$ and $R_5$ may be identical or different; $R_6$ is a hydrogen atom, a lower alkyl radical or a radical —CO—$R_9$ and further wherein the radicals $R_6$ may be identical or different; $R_7$ is (a) a hydrogen atom, (b) a lower alkyl radical, (c) a radical of the formula:

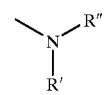

or a (d) a radical —$OR_8$ wherein $R_8$ is a hydrogen atom, a linear or branched alkyl radical having from 1 to 20 carbon atoms, an alkenyl radical, a mono- or polyhydroxyalkyl radical, or a phenyl, benzyl or phenethyl radical, which are optionally substituted by at least one halogen atom, or a hydroxyl or nitro functional group; $R_9$ is a lower alkyl radical; $R_{10}$ is a hydrogen atom, a lower alkyl radical, or a radical —$OR_6$; $R_{11}$ is a radical —$OR_6$; R' and R", which may be identical or different, are each a hydrogen atom, a lower alkyl radical, a mono or polyhydroxyalkyl radical or a phenyl radical optionally substituted by at least one halogen atom, or a hydroxyl or nitro functional group, or R' and R" together with the nitrogen atom attached may form a piperidino, morpholino, pyrrolidino or piperazino radical which are optionally substituted at the 4-position by a $C_1$–$C_6$ alkyl radical or a mono- or polyhydroxyalkyl radical; t is an integer equal to 0, 1 or 2; and the radicals $R_{10}$ and $R_{11}$ may together form a single oxo group of the forumla=O; or pharmaceutically/cosmetically acceptable salt or optical or geometric isomer thereof.

2. The method defined by claim 1, wherein the dermatological disorder is treated.

3. The method defined by claim 1, wherein the ophthalmological disorder is treated.

4. The method as defined by claim 1, wherein the skin aging is treated.

5. The method as defined by claim 1, wherein the epidermal and/or dermal atrophy is treated.

6. The method as defined by claim 1, wherein the cicatrization disorder is treated.

7. The method as defined by claim 1, wherein the sebaceous function disorder is treated.

8. The method as defined by claim 1, wherein the cancerous or precancerous disease state is treated.

9. The method as defined by claim 1, wherein the inflammation is treated.

10. The method as defined by claim 1, wherein the viral infection is treated.

11. The method as defined by claim 1, wherein alopecia is treated or prevented.

12. The method as defined by claim 1, wherein the cardiovascular disorder is treated.

13. The method as defined by claim 1, wherein the immune deficiency is treated.

14. The method as defined by claim 1, wherein the dermatological, rheumatic, respiratory, cardiovascular or ophthalmologic disorder is treated.

15. The method as defined by claim 14, comprising administering to such organism a daily dose of said polyaromatic propynyl compound of about 0.01 mg/kg to 100 mg/kg of body weight thereof.

16. A method for treating a skin or hair disorder on a mammalian organism in need of such treatment, comprising administering to such organism a cosmetically/therapeutically effective amount of a pharmaceutical composition of matter, which comprises a cosmetically effective amount of a polyaromatic propynyl compound or cosmetically acceptable salt or isomer thereof, wherein the polyaromatic propynyl compound has the structural formula (I):

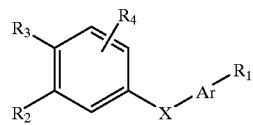

(I)

in which X is one of the radicals:

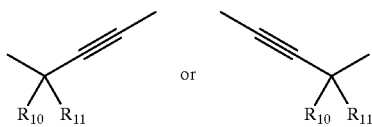

Ar is a radical of the following formula (a):

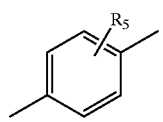

(a)

$R_1$ (i) a hydrogen atom, (ii) a radical —$CH_2$, (iii) a radical —$CH_2$—O—$R_6$, (iv) a radical —O—$R_6$; (v) a radical —CO—$R_7$, or (vi) a radical —S(O)$_t$$R_9$; $R_2$ and $R_3$ together form, with the carbon atoms from which they depend, a 5- or 6membered ring optionally substituted by methyl groups and/or optionally interrupted by an oxygen or sulfur atom; $R_4$ is a hydrogen atom a halogen atom, a lower alkyl radical or a radical —O$R_6$; $R_5$ has the definition of $R_4$, and $R_4$ and $R_5$ may be identical or different; $R_6$ is a hydrogen atom, a lower alkyl radical or a radical —CO—$R_9$ and further wherein the radicals $R_6$ may be identical or different; $R_7$ is (a) a hydrogen atom, (b) a lower alkyl radical, (c) a radical of the formula:

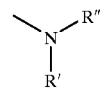

or (d) a radial —O$R_8$ wherein $R_8$ is a hydrogen atom, a linear or branched alkyl radical having from 1 to 20 carbon atoms, an alkenyl radical, a mono- or polyhydroxyalkyl radical, or a phenyl, benzyl or phenethyl radical, which are optionally substituted by at least one halogen atom, or a hydroxyl or nitro functional group; $R_9$ is a lower alkyl radical; $R_{10}$ is a hydrogen atom, a lower alkyl radical, or a radical —O$R_6$; $R_{11}$ is a radical —O$R_6$; R' and R", which may identical or different, are each a hydrogen atom, a lower alkyl radical, a mono or polyhydroxyalkyl radical, or a phenyl radical optionally substituted by at least one halogen atom, or a hydroxyl or nitro functional group, or R' and R" together with the nitrogen atom attached may form a piperidino, morpholino, pyrrolidino or piperazino radical which are optionally substituted at the 4-position by a $C_1$–$C_6$ alkyl radical or mono- or polyhydroxyalkyl radical; t is an integer equal to 0, 1 or 2; and the radicals $R_{10}$ and $R_{11}$ may together form a single oxo group of the formula=O; or pharmaceutically/cosmetically acceptable salt or optical or geometric isomer thereof.

17. The method according to claim 2, wherein the dermatological disorder is selected from the group consisting of acne vulgaris, comedo-type acne, polymorphic acne, rosacea acne, nodulocystic acne, acne conglobata, senile acne and a secondary acne.

18. The method according to claim 7, wherein the secondary acne is selected from the group consisting of solar acne, acne medicamentosa and occupational acne.

19. The method as defined by claim 1, wherein the keratinization disorder is treated.

20. A method for treating a keratinization disorder, a dermatological disorder, an ophthalmological disorder, skin aging, epidermal and/or dermal atrophy a cicatrization disorder, a sebaceous function disorder, a cancerous or precancerous disease state, inflammation, a viral infection, alopecia, a cardiovascular disorder, an immune deficiency, a rheumatic disorder, or a respiratory disorder, in a mammalian organism in need of such treatment, comprising administering to such organism a therapeutically effective amount of a pharmaceutical composition of matter which comprises a therapeutically effective amount of a polyaromatic propynyl compound or a pharmaceutically acceptable salt or isomer thereof, wherein the polyaromatic propynyl compound has the structural formula (I):

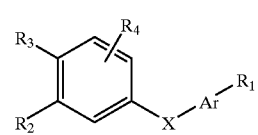

(I)

in which X is one of the radicals:

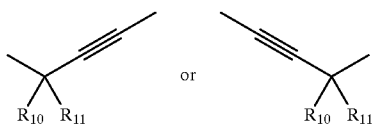

wherein $R_{10}$ and $R_{11}$ are as defined below; Ar is a radical of the following formula (a):

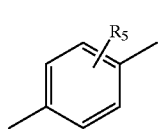

wherein $R_5$ and $R_6$ are defined below; $R_1$ is (i) a hydrogen atom, (ii) a radical —$CH_3$, (iii) a radical —$CH_2$—O—$R_6$, (iv) a radical —O—$R_6$, (v) a radical —CO—$R_6$, or (vi) a radical —$S(O)_tR_9$; $R_2$ and $R_3$, which may be identical or different, are each a hydrogen atom, a linear or branched alkyl radical having from 1 to 20 carbon atoms, a radical —$OR_6$ or a radical —$SR_6$, with the proviso that $R_2$ and $R_3$ may together form, with the carbon atoms from which they depend, a 5- or 6-membered ring optionally substituted by methyl groups and/or optionally interrupted by an oxygen or sulfur atom; $R_4$ is a hydrogen atom, a halogen atom, a lower alkyl radical or a radical —$OR_6$; $R_5$ has the definition of $R_4$, with the proviso that $R_4$ and $R_5$ may be identical or different; $R_6$ is a hydrogen atom, a lower alkyl radical or a radical —CO—$R_9$ and further wherein the radicals $R_6$ may be identical or different; $R_7$ is (a) a hydrogen atom, (b) a lower alkyl radical, (c) a radical of the formula:

R' and R" are as defined below, or (d) a radical —$OR_8$ wherein $R_8$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue, or an amino acid or peptide residue; $R_9$ is a lower alkyl radical; $R_{10}$ is a hydrogen atom, a lower alkyl radical, or a radical —$OR_6$; $R_{11}$ is a radical —$OR_6$; R' and R", which may be identical or different, are each a hydrogen atom, a lower alkyl radical, a mono or polyhydroxyalkyl radical, an optionally substitued aryl radical or an amino acid or peptide or sugar residue, with the privoso that R' and R" together with the nitrogen atom attached may form a heterocycle; t is an integer equal to 0, 1 or 2; and with the further proviso that the radicals $R_{10}$ and $R_{11}$ may together form a single oxo group of the formula=O; or pharmaceutically/cosmetically acceptable salt or optical or geometric isomer therof; with the proviso that (1) when $R_{10}$ is a hydrogen atom and $R_{11}$ is —OH or when the radicals $R_{10}$ and $R_{11}$ together form a single oxo group of the formula=O, and when $R_2$ and $R_3$ do not form a 5- or 6-membered ring, then $R_4$ is not —OH when $R_4$ is in the ortho position on the ring with respect to X, $R_5$ is not —OH when $R_5$ is in the ortho position on the ring with respect to X, and $R_1$ is not a hydrogen atom, a radical —$CH_3$ or a radical —O—$R_6$ is a lower alkyl radical;

(2) if $R_{10}$ represents a hydrogen atom, $R_{11}$ is a hydroxyl radical and $R_2$ and $R_3$ do not form, with the adjacent aromatic ring, 5- or 6- membered ring, then $R_4$ does not represent a hydroxyl radical when $R_4$ is in a position ortho to the α position of the ring;

3) if $R_{10}$ represents a hydrogen atom and $R_{11}$ a hydroxyl radical, or $R_{10}$ and $R_{11}$ together form a single oxo radical of formula=O, and $R_2$ and $R_3$ do not form, with the adjacent aromatic ring, a 5- or 6-membered ring, then $R_5$ does not represent a hydroxyl radical when $R_5$ is in a position ortho to the α position of the Ar ring of formula (a);

(4) if $R_{10}$ represents a hydrogen atom and $R_{11}$ is a hydroxyl radical, or $R_{10}$ and $R_{11}$ form a single oxo radical of formula=O; $R_2$ and $R_3$ do not form, with the adjacent aromatic ring, a 5- or 6-membered ring; and Ar is a radical of formula (a); then $R_1$ does not represent (i), (ii) or (iv) if $R_6$ is a $C_1$–$C_6$ alkyl radical; and (5) if $R_{10}$ and $R_{11}$ form a single oxo radical of formula=O, Ar is a radical of formula (a), and $R_2$ and $R_3$ together form, with the adjacent aromatic ring, a naphthyl radical, then $R_1$ is different than (i).

21. The method as defined by claim 20, wherein the keratinization disorder is treated.

22. The method as defined by claim 20, wherein the dermatological disorder is treated.

23. The method as defined by claim 20, wherein the ophthalmological disorder is treated.

24. The method as defined by claim 20, wherein the skin aging is treated.

25. The method as defined by claim 20, wherein the epidermal and/or dermal atrophy is treated.

26. The method as defined by claim 20, wherein the cicatrization disorder is treated.

27. The method as defined by claim 20, wherein the sebaceous function disorder is treated.

28. The method as defined by claim 20, wherein the cancerous or precancerous disease state is treated.

29. The method as defined by claim 20, wherein the inflammation is treated.

30. The method as defined by claim 20, wherein the viral infection is treated.

31. The method as a defined by claim 20, wherein alopecia is treated or prevented.

32. The method as defined by claim 20, wherein the cardiovascular disorder is treated.

33. The method as defined by claim 20, wherein the immune deficiency is treated.

34. The method as defined by claim 20, wherein the dermatological, rheumatic, respiratory, cardiovascular or ophthalmologic disorder is treated.

35. A method for treating a skin or hair disorder on a mammalian organism in need of such treatment, comprising administering to such organism a cosmetically/therapeutically effective amount of a pharmaceutical composition of matter which comprises a cosmetically effective amount of a polyaromatic propynyl compound or cosemetically acceptable salt or isomer thereof, wherein the polyaromatic propynyl compound has the structural formula (I):

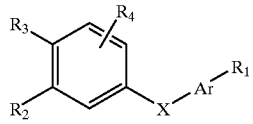

(I)

in which X is one of the radicals:

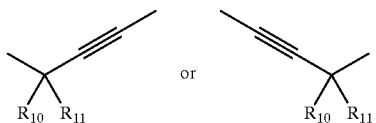

wherein $R_{10}$ and $R_{11}$ are as defined below; Ar is a radical of the following formula (a):

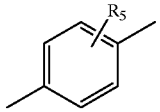

(a)

wherein $R_5$ and $R_6$ are as defined below; $R_1$ is (i) a hydrogen atom, (ii) a radical —$CH_3$, (iii) a radical —$CH_2$—O—$R_6$, (iv) a radical —O—$R_6$, (v) a radical —CO—$R_7$, or (vi) a radical —$S(O)_tR_9$; $R_2$ and $R_3$, which may be identical or different, are each a hydrogen atom, a linear or branched alkyl radical having from 1 to 20 carbon atoms, a radical —$OR_6$ or a radical —$SR_6$, with the proviso that $R_2$ and $R_3$ may together form, with the carbon atoms from which they depend, a 5- or 6-membered ring optionally substitued by methyl groups and/or optionally interrupted by an oxygen or sulfur atom; $R_4$ is a hydrogen atom, a halogen atom, a lower alkyl radical or a radical —$OR_6$; $R_5$ has the definition of $R_4$, with the proviso that $R_4$ and $R_5$ may be identical or different; $R_6$ is a hydrogen atom, a lower alkyl radical or a radial —CO—$R_9$ and further wherein the radicals $R_6$ may be identical or different; $R_7$ is (a) a hydrogen atom, (b) a lower alkyl radical (c) a radical of the formula:

wherein R' and R" are as defined below, or (d) a radical —$OR_8$ wherein $R_8$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue, or an amino acid or peptide residue; $R_9$ is a lower alkyl radical; $R_{10}$ is a hydrogen atom, a lower alkyl radical, or a radical —$OR_6$; $R_{11}$ is a radical —$OR_6$; R' and R", which may be identical or different, are each a hydrogen atom, a lower alkyl radical, a mono or polyhydroxyalkyl radical, an optionally substituted aryl radical or an amino acid or peptide or sugar residue, with the proviso that R' and R" together with the nitrogen atom attached may form a heterocycle; t is an integer equal to 0, 1 or 2; and with the further proviso that the radicals $R_{10}$ and $R_{11}$ may together form a single oxo group of the formula=O; or pharmaceutically/cosmetically acceptable salt or optical or geometric isomer thereof; with the proviso that (1) when $R_{10}$ is a hydrogen atom and $R_{11}$ is —OH or when the radicals $R_{10}$ and $R_{11}$ together form a single oxo group of the formula=O, and when $R_2$ and $R_3$ do not form a 5- or 6-membered ring, then $R_4$ is not —OH when $R_4$ is in the ortho position on the ring with respect to X, $R_5$ is not —OH when $R_5$ is in the ortho position on the ring with respect to X, and $R_1$ is not a hydrogen atom, a radical —$CH_3$ or a radical —O—$R_6$ where $R_6$ is a lower alkyl radical;

(2) if $R_{10}$ represents a hydrogen atom, $R_{11}$ is a hydroxyl radical and $R_2$ and $R_3$ do not form, with the adjacent aromatic ring, 5- or 6-membered ring, then $R_4$ does not represent a hydroxyl radical when $R_4$ is in a position ortho to the α position of the ring;

(3) if $R_{10}$ represents a hydrogen atom and $R_{11}$ a hydroxyl radical, or $R_{10}$ and $R_{11}$ together form a single oxo radical of formula=O, and $R_2$ and $R_3$ do not form, with the adjacent aromatic ring, a 5- or 6-membered ring, then $R_5$ does not represent a hydroxyl radical when $R_5$ is in a position ortho to the α position of the Ar ring of formula (a);

(4) if $R_{10}$ represents a hydrogen atom and $R_{11}$ is a hydroxyl radical, or $R_{10}$ and $R_{11}$ form a single oxo radical of formula=O; $R_2$ and $R_3$ do not form, with the adjacent aromatic ring, a 5- or 6- membered ring; and Ar is a radical of formula (a); then $R_1$ does not represent (i), (ii) or (iv) if $R_6$ is a $C_1$–$C_6$ alkyl radical; and (5) if $R_{10}$ and $R_{11}$ form a single oxo radical of formula=O, Ar is a radical of formula (a), and $R_2$ and $R_3$ together form, with the adjacent aromatic ring, a naphythyl radical, then $R_1$ is different than (i).

36. The method as defined by claim 1, wherein the pharmaceutical composition of matter further comprises a pharmaceutically acceptable carrier or diluent therefor.

37. The method as defined by claim 16, wherein the pharmaceutical composition of matter further comprises a pharmaceutically acceptable carrier or diluent therefor.

38. The method as defined by claim 20, wherein the pharmaceutical composition of matter further comprises a pharmaceutically acceptable carrier or diluent therefor.

39. The method as defined by claim 35, wherein the pharmaceutical composition of matter further comprises a pharmaceutically acceptable carrier or diluent therefor.

* * * * *